(12) United States Patent
Poyss et al.

(10) Patent No.: US 10,695,157 B2
(45) Date of Patent: Jun. 30, 2020

(54) PACKAGING SYSTEM FOR TISSUE GRAFTS

(71) Applicant: MUSCULOSKELETAL TRANSPLANT FOUNDATION, Edison, NJ (US)

(72) Inventors: Elizabeth Ann Poyss, Medford, NJ (US); Todd J. Nilsen, Howell, NJ (US); Alison Ling, Piscataway, NJ (US); Kevin Wu, Morganville, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 440 days.

(21) Appl. No.: 15/402,806

(22) Filed: Jan. 10, 2017

(65) Prior Publication Data
US 2018/0193127 A1 Jul. 12, 2018

(51) Int. Cl.
*A61F 2/00* (2006.01)
*A01N 1/02* (2006.01)
*B65B 25/00* (2006.01)
*B65B 9/04* (2006.01)

(52) U.S. Cl.
CPC .......... *A61F 2/0095* (2013.01); *A01N 1/0263* (2013.01); *A01N 1/0268* (2013.01); *B65B 9/042* (2013.01); *B65B 25/00* (2013.01); *A01N 1/0273* (2013.01); *A61F 2/0063* (2013.01); *B65B 2220/16* (2013.01)

(58) Field of Classification Search
CPC ... A61F 2/0095; A61F 2/0063; A01N 1/0268; A01N 1/0273; A01N 1/0263
See application file for complete search history.

(56) References Cited

U.S. PATENT DOCUMENTS

| | | |
|---|---|---|
| 2,022,906 A | 12/1935 | Weeks |
| 2,981,405 A | 4/1961 | Grasty |
| 3,346,168 A | 10/1967 | Rouder |
| D216,171 S | 11/1969 | Murr |
| 3,776,411 A | 12/1973 | Luckadoo |

(Continued)

FOREIGN PATENT DOCUMENTS

| | | | |
|---|---|---|---|
| DE | 19725499 A1 * | 12/1998 | ......... A61F 25/0095 |
| EP | 1943975 | 7/2008 | |

OTHER PUBLICATIONS

Machine Translation of DE 19725499 A1 (Year: 2019).*

(Continued)

*Primary Examiner* — Michael L Hobbs
(74) *Attorney, Agent, or Firm* — Marcella M. Bodner; Cole Schotz, P.C.

(57) ABSTRACT

A tissue graft packaging system having a retainer including first and second members with respective first and second pluralities of channel sidewalls that define first and second pluralities of channels, and first and second engagement means configured to removeably interconnect the first and second members. The first and second pluralities of channel sidewalls are configured to create a continuous interior space between the first and second members. A tissue graft, such as a cryopreserved viable tissue graft, is contained within the continuous interior space of the retainer. Processes for packaging, thawing and rinsing the tissue graft using the tissue graft packaging system and its retainer are also disclosed.

40 Claims, 11 Drawing Sheets
(3 of 11 Drawing Sheet(s) Filed in Color)

(56) References Cited

U.S. PATENT DOCUMENTS

| | | |
|---|---|---|
| 4,046,311 A | 9/1977 | Voytko |
| 4,391,863 A | 7/1983 | Bonis |
| 4,674,676 A | 6/1987 | Sandel et al. |
| 4,697,703 A | 10/1987 | Will |
| 4,714,595 A | 12/1987 | Anthony et al. |
| 4,736,850 A | 4/1988 | Bowman et al. |
| 4,750,619 A | 6/1988 | Cohen et al. |
| 4,763,791 A | 8/1988 | Halverson et al. |
| D299,955 S | 2/1989 | Kendrick |
| 4,850,488 A | 7/1989 | Humbert |
| 4,863,052 A | 9/1989 | Lambert |
| 4,867,372 A | 9/1989 | Patterson |
| D305,478 S | 1/1990 | Lahm et al. |
| 5,040,677 A | 8/1991 | Tubo et al. |
| 5,176,258 A | 1/1993 | Antal |
| 5,193,679 A | 3/1993 | White |
| 5,257,692 A | 11/1993 | Heacox |
| 5,494,162 A | 2/1996 | Treace et al. |
| 5,503,324 A | 4/1996 | Bacchetti et al. |
| D371,047 S | 6/1996 | Houyou |
| 5,615,770 A | 4/1997 | Applebaum et al. |
| 5,645,527 A | 7/1997 | Beck |
| 5,690,226 A | 11/1997 | N'Guyen |
| 5,720,391 A | 2/1998 | Dohm et al. |
| 5,772,031 A | 6/1998 | Landis |
| 5,868,253 A | 2/1999 | Krueger et al. |
| 5,924,625 A | 7/1999 | Klein et al. |
| 5,954,202 A | 9/1999 | Mellon |
| 6,012,580 A | 1/2000 | Peters et al. |
| 6,039,183 A | 3/2000 | Rudnick et al. |
| D444,060 S | 6/2001 | Eisner |
| D447,946 S | 9/2001 | Tsurushi et al. |
| D450,240 S | 11/2001 | Haag et al. |
| 6,622,864 B1 | 9/2003 | Debbs et al. |
| 6,629,602 B1 | 10/2003 | Heyman |
| 6,830,149 B2 | 12/2004 | Merboth et al. |
| 6,854,599 B2 | 2/2005 | Ferrara |
| D510,262 S | 10/2005 | Isono |
| D510,263 S | 10/2005 | Isono et al. |
| 7,162,850 B2 | 1/2007 | Marino et al. |
| 7,316,318 B1 | 1/2008 | Rosten et al. |
| 7,320,404 B2 | 1/2008 | Landis |
| D598,282 S | 8/2009 | Abrahamsson |
| 7,648,030 B2 | 1/2010 | Landis |
| D612,594 S | 3/2010 | Wade |
| 7,669,716 B2 | 3/2010 | Lightner et al. |
| D613,418 S | 4/2010 | Ryan |
| D638,137 S | 5/2011 | Gross |
| D642,904 S | 8/2011 | Turvey |
| 8,006,839 B2 | 8/2011 | Hafner |
| 8,240,477 B2 | 8/2012 | Lightner et al. |
| 8,365,910 B2 | 2/2013 | Valaie et al. |
| D679,586 S | 4/2013 | Afford et al. |
| D718,471 S | 11/2014 | So et al. |
| D718,472 S | 11/2014 | So |
| 8,893,883 B2 | 11/2014 | Valaie et al. |
| 8,966,867 B2 | 3/2015 | Liccardo et al. |
| 91,444,464 | 9/2015 | Knowlton et al. |
| D742,222 S | 11/2015 | Liu |
| D755,986 S | 5/2016 | Green |
| D766,368 S | 9/2016 | Kiosky |
| D776,823 S | 1/2017 | Duan-Arnold et al. |
| 9,851,349 B2 | 12/2017 | Musat |
| D829,566 S | 10/2018 | Safdie |
| D832,457 S | 10/2018 | Poyss |
| D843,586 S | 3/2019 | Duan-Arnold et al. |
| D843,587 S | 3/2019 | Duan-Arnold et al. |
| D844,150 S | 3/2019 | Duan-Arnold et al. |
| 2002/0112981 A1 | 8/2002 | Cooper et al. |
| 2003/0336781 | 12/2003 | Liao |
| 2004/0132205 A1 | 7/2004 | Moon |
| 2004/0224298 A1* | 11/2004 | Brassil ............... A01N 1/02 435/1.1 |
| 2005/0186373 A1 | 8/2005 | Rhee et al. |
| 2005/0186376 A1 | 8/2005 | Rhee et al. |
| 2005/0242017 A1 | 11/2005 | Staats |
| 2005/0269231 A1 | 12/2005 | White et al. |
| 2010/0009459 A1 | 1/2010 | Herminghaus |
| 2010/0155282 A1 | 6/2010 | Govil |
| 2011/0139661 A1 | 6/2011 | Ludwig |
| 2012/0021151 A1 | 1/2012 | Tatarka et al. |
| 2012/0208273 A1 | 8/2012 | Tarunina |
| 2013/0233736 A1 | 9/2013 | Hess et al. |
| 2013/0327667 A1 | 12/2013 | Grabowski |
| 2014/0073004 A1 | 3/2014 | Williamson |
| 2014/0090999 A1 | 4/2014 | Kirsch |
| 2014/0134302 A1 | 5/2014 | Hodge |
| 2014/0135236 A1 | 5/2014 | Musat |
| 2014/0202908 A1 | 7/2014 | Liburd |
| 2014/0299498 A1 | 10/2014 | Neal et al. |
| 2015/0076023 A1* | 3/2015 | Kinyon ............ A61F 2/0095 206/438 |
| 2015/0259119 A1 | 9/2015 | Duan-Arnold |
| 2015/0351893 A1 | 12/2015 | Smith |
| 2016/0066998 A1 | 3/2016 | Knowlton et al. |
| 2016/0135895 A1 | 5/2016 | Faasse et al. |
| 2016/0166369 A1 | 6/2016 | Anderson |
| 2016/0228231 A1 | 8/2016 | Southard et al. |
| 2016/0324797 A1 | 11/2016 | Allen |
| 2018/0263239 A1 | 9/2018 | Sinclair et al. |

OTHER PUBLICATIONS

Design U.S. Appl. No. 29/619,999, filed Oct. 3, 2017, entitled "Tissue Graft Retainer" (11 pages).
Office Action for U.S. Appl. No. 15/913,448 dated Feb. 6, 2019.
U.S. Appl. No. 15/913,448, filed Mar. 6, 2018.
Non-Final Office Action for Design U.S. Appl. No. 29/590,395, dated Apr. 3, 2018.
Non-Final Office Action for Design U.S. Appl. No. 29/619,999, dated Dec. 10, 2018.
Design U.S. Appl. No. 29/590,395, filed Jan. 10, 2017.
Design U.S. Appl. No. 29/619,999, filed Oct. 3, 2017.
Non-Final Office Action for U.S. Appl. No. 15/913,448, dated Aug. 6, 2019.

* cited by examiner

PACKAGING SYSTEM FOR TISSUE GRAFTS

FIELD OF THE INVENTION

The present invention relates generally to packaging for tissue grafts, and in particular, to packaging systems that include a tissue graft retainer for tissue grafts.

SUMMARY OF THE INVENTION

The present invention is directed to a tissue graft packaging system having a retainer. The retainer includes a first member having a first inner surface including first engagement means, a first plurality of channel sidewalls extending along the first inner surface, and a first plurality of channels defined by the first plurality of channel sidewalls, and a second member having a second inner surface including second engagement means configured to removeably engage the first engagement means, a second plurality of channel sidewalls extending along the second inner surface, and a second plurality of channels defined by the second plurality of channel sidewalls. The first and second pluralities of channel sidewalls are configured to form a continuous interior space between the first and second members.

The present invention is also directed to processes for packaging, thawing and rinsing cryopreserved viable tissue grafts using the tissue graft packaging system and its retainer, wherein the retainer has at least one first side passageway and at least one end passageway. The packaging process includes the steps of providing a viable tissue graft; placing a backing on the viable tissue graft such that the backing is maintained in contact with the viable tissue graft; placing the viable tissue graft and the backing on the first inner surface of the first member to engage the first channel sidewalls thereof and contact the plurality of first channels; securing the first and second members together via the first and second engagement means, whereby the viable tissue graft is contained within the continuous interior space between the first and second members, and wherein the first and second members (and their respective components) are configured such that they minimally contact the viable tissue graft. The packaging process further includes the steps of introducing cryopreservation media into the retainer via said first and second pluralities of channels to immerse the viable tissue graft in cryopreservation media; and cryopreserving the viable tissue graft. The thawing and rinsing process includes the steps of thawing the viable tissue graft within the retainer; removing the cryopreservation media from the retainer via the first side passageway(s) and end passageway(s); and rinsing the retainer and viable tissue graft therein.

BRIEF DESCRIPTION OF THE DRAWINGS

The patent application file contains at least one drawing executed in color. Copies of this patent application publication with color drawing(s) will be provided by the Office upon request and payment of the necessary fee.

The present invention will be further explained with reference to the attached drawings, wherein like structures are referred to by like numerals throughout the several views. The drawings shown are not necessarily to scale, with emphasis instead generally being placed upon illustrating the principles of the present invention.

DETAILED DESCRIPTION OF THE INVENTION

Detailed embodiments of the present invention are disclosed herein. It should be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, and some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as examples for teaching one skilled in the art to variously employ the present invention.

The present invention generally relates to a packaging system for the storage, containment and transportation of tissue grafts (e.g., allografts, autografts, xenografts, tissue-engineered grafts, etc.), and in particular, tissue grafts that are cryopreserved (i.e., tissue grafts that are maintained in cryopreservation media) to maintain at least a portion of their viability. The description of the packaging system and retainer of the present invention are described below. The packaging system may also be employed with non-cryopreserved tissue grafts, as discussed below.

Figure 1:
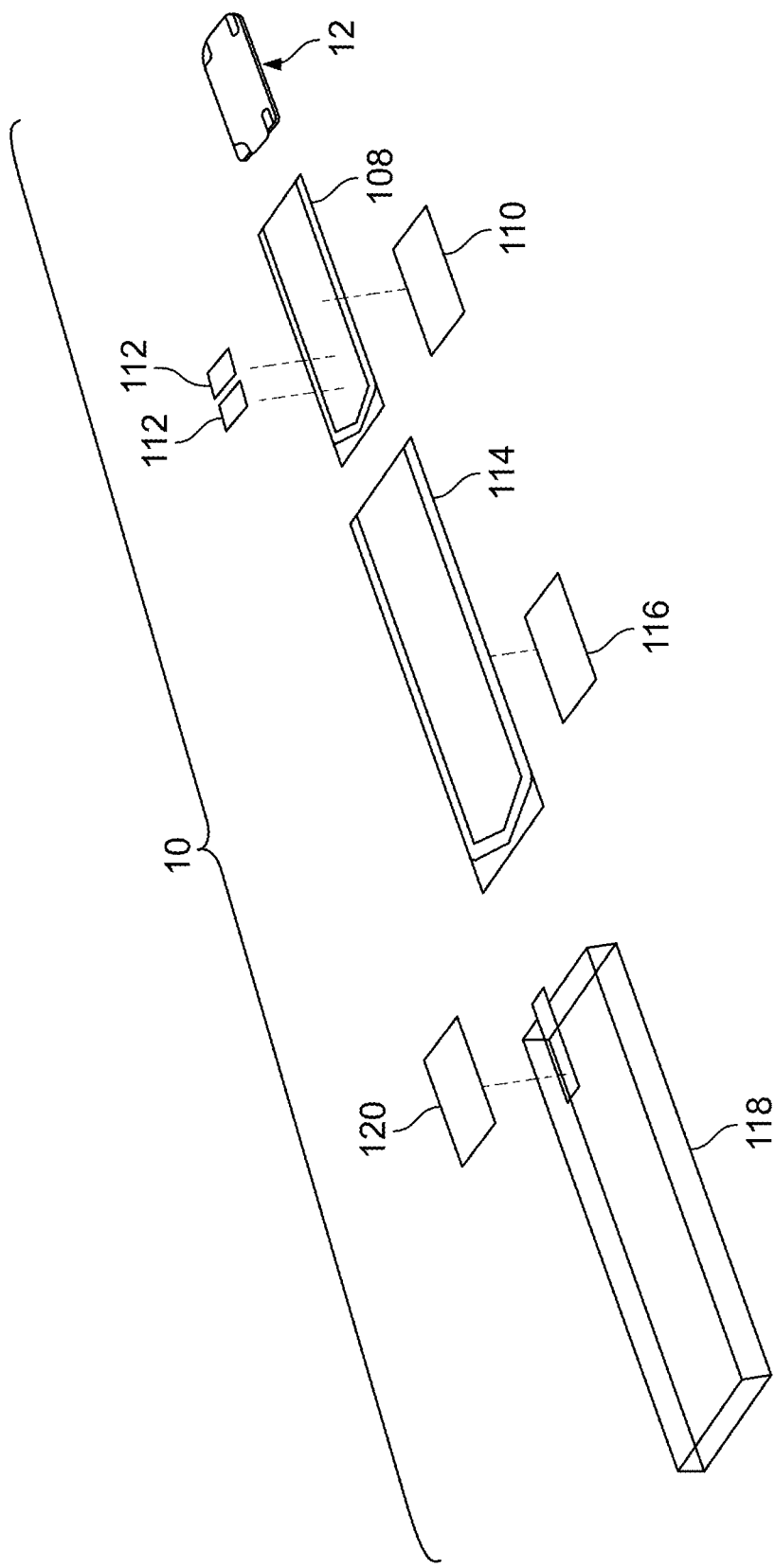
FIG. 1 is a perspective, exploded view of a tissue graft packaging system in connection with an embodiment of the present invention.

An embodiment of the packaging system 10 of the present invention is schematically shown in FIG. 1, and includes a retainer 12 and other components that are described below. As further disclosed below, the retainer 12 holds a cryopreserved tissue graft securely therein, but is also constructed with features that enable cryopreservation media to flow to the tissue graft and suspend the tissue graft therein, which protects the viable cells of the tissue graft throughout its shelf life. Such a tissue graft may include, for example, a viable allograft dermis graft. In another embodiment, the retainer may also hold a non-cryopreserved (i.e., dehydrated, lyophilized, refrigerated etc.) tissue graft. It is understood that in any of the non-cryopreserved configurations of the tissue graft, the cryopreservation media may be replaced with any media/solution compatible to the tissue graft, regardless of whether or not the solution has cryopreservation capabilities. Further, it is understood that in any of the non-cryopreserved configurations of the tissue graft, the cryopreservation media may be omitted and not replaced, thus creating a configuration of the tissue graft without any media/solution present.

Figure 2:
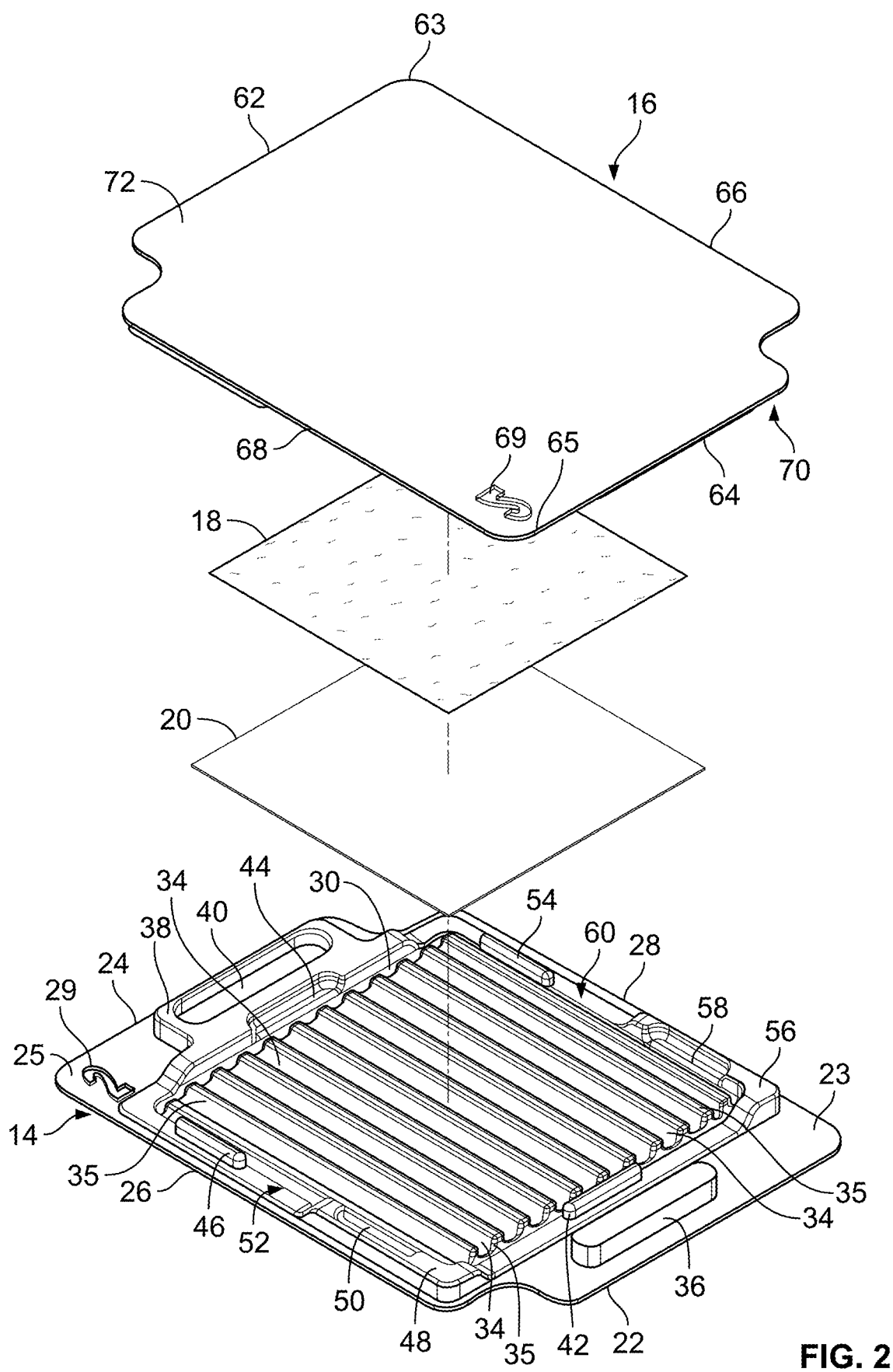
FIG. 2 is a perspective, exploded view of a tissue graft retainer used with the packaging system of FIG. 1, along with a tissue graft and backing therefor, all according to the present invention.

Referring now to FIG. 2, one embodiment of the retainer 12 of the present invention is illustrated, including a first member 14 and a separate second member 16 that cooperate to engage one another and contain a tissue graft 18 and, optionally, a backing 20 for the tissue graft 18. In this embodiment, the first and second members 14, 16 are separate, and not permanently connected to one another, such as by a hinge. Providing the first and second members 14, 16 as separate from one another prevents bowing of the retainer 12 when subjected to cryopreservation temperatures, and thereby enables the retainer 12 to remain closed in a relatively flat configuration to retain the tissue graft 18 therein.

In an embodiment, the first and second members 14, 16 are structurally identical to one another (i.e., having the same structural features, dimensions, configurations and shapes as one another). The first member 14 of this embodiment is further described below, with the understanding that the description is also applicable to the second member 16.

In alternate embodiments, the first and second members 14, 16 are not structurally identical. In both embodiments where the first and second members 14, 16 are and are not structurally identical, the structure of the first member 14 may be symmetrical to the structure of the second member 16. More particularly, in being symmetrical to each other, the first and second members 14, 16 correspond in size, shape, and relative position of their respective structural features on opposite sides of a median plane and/or a dividing line between them, and thereby fit together to engage one another in a symmetrical fashion. The first and second members 14, 16 may therefore engage one another via their respective structural features, whether identical, symmetrical, or both, as further described below.

In the embodiment illustrated in FIGS. 1-12, the first and second members 14, 16 (which are structurally identical) are arranged to be symmetrical to one another in that their respective surfaces (and associated structural features) are inverted with respect to one another on opposite sides of a median plane that is substantially parallel to the surfaces of the first and second members 14, 16.

With reference to FIGS. 2-5, the first member 14 of the retainer 12 illustrated in FIG. 2 is substantially planar, and includes a first end 22 having a first corner tab 23, an opposed second end 24 having a second corner tab 25, and opposed first and second sides 26, 28 extending between the first and second ends 22, 24. In an embodiment, the first corner tab 23, second corner tab 25 and all other corners and edges of the first member 14 are rounded, so as to avoid puncturing the pouches in which the retainer 12 is contained. Such pouches are described below.

In an embodiment, the second corner tab 25 includes first indicia 29, for purposes of correctly aligning the first member 14 with the second member 16 when assembling the retainer 12, as further described below. The first indicia 29 may be an alphanumeric symbol (e.g., the numeral 2, as shown in FIGS. 2 and 3) or other symbol that can be readily identified during packaging of the tissue graft.

Figure 3:
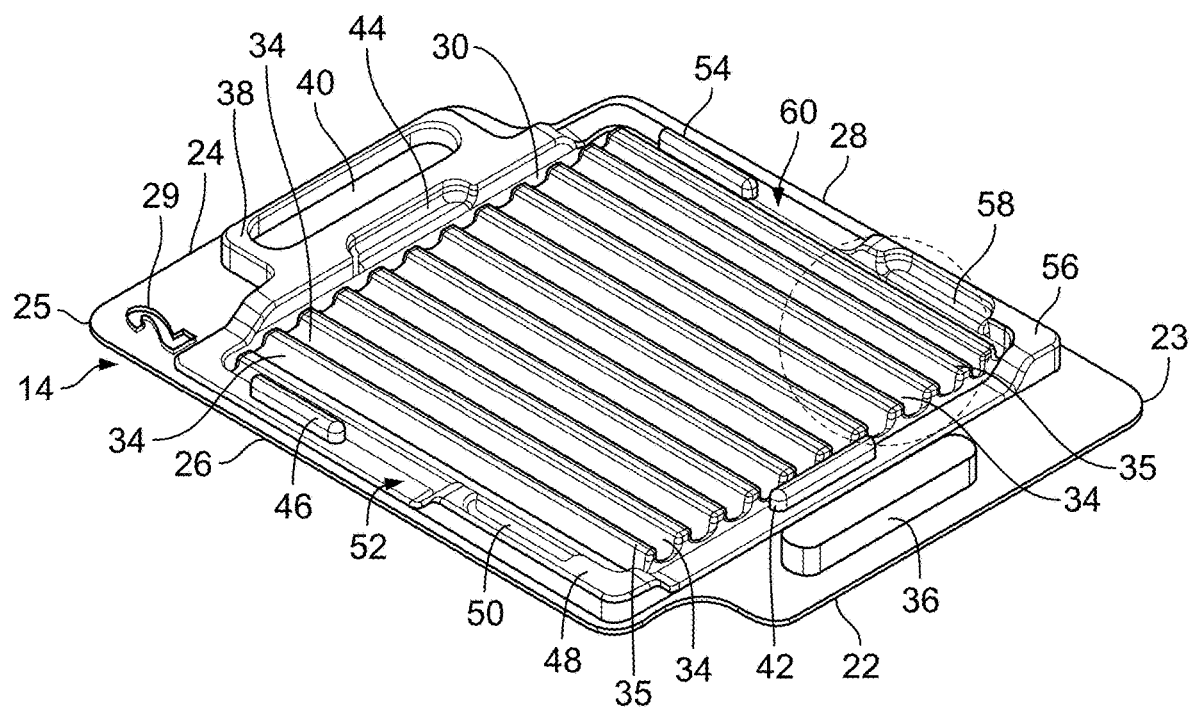
FIG. 3 is a perspective view of a first member of the tissue graft retainer of FIG. 2.
Figure 3A:
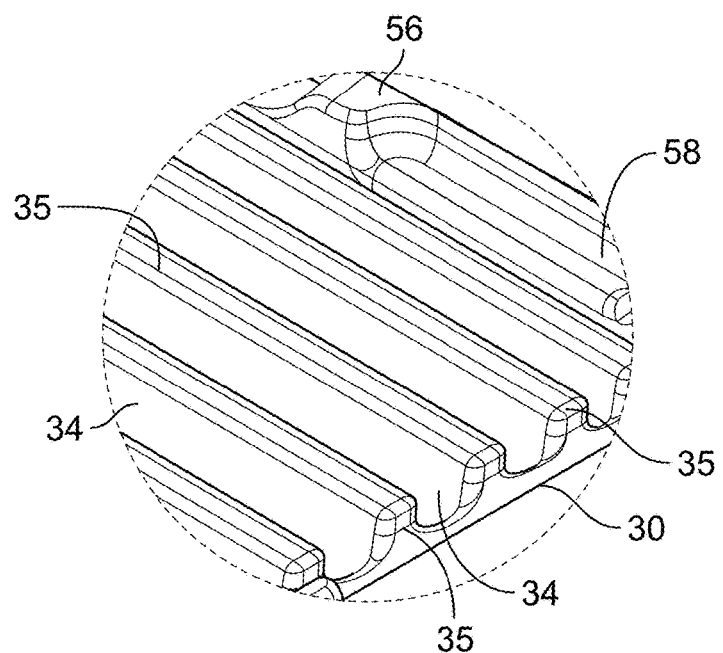
FIG. 3A is an enlarged perspective view of a portion of the first member of the tissue graft retainer of FIG. 3.
Figure 4:
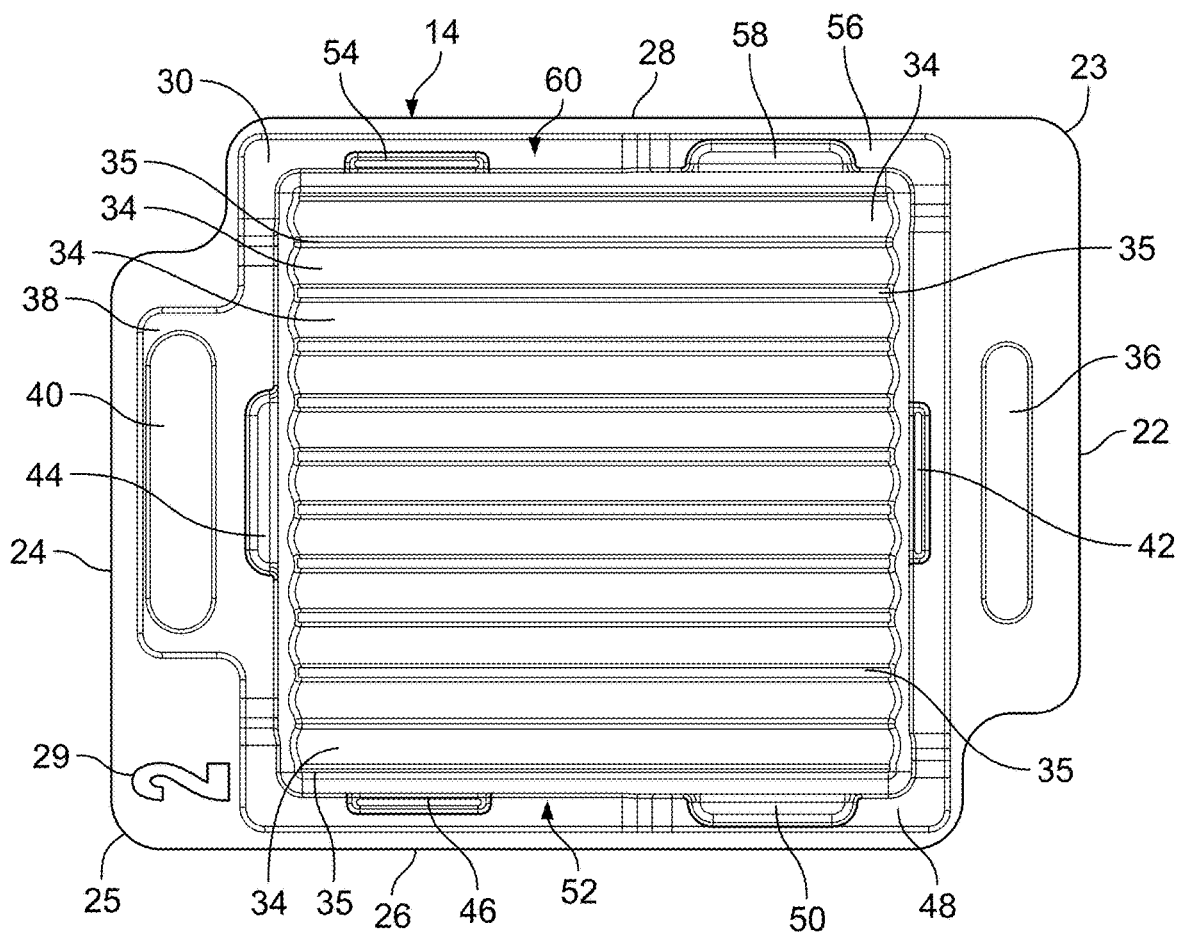
FIG. 4 is a top plan view of the first member of the tissue graft retainer of FIG. 2.

The first member 14 further includes a first inner surface 30 that is positioned proximate the graft 18 upon assembly of the retainer 12 of the packaging system 10, and a first outer surface 32 that is a positioned distal the tissue graft 18 upon assembly of the retainer 12 (see FIGS. 2-5). The first inner surface 30 includes a first plurality of channels 34 that extend longitudinally between the first and second ends 22, 24 of the first member 14 (see FIGS. 2-4). The first channels 34 are defined by a first plurality of channel sidewalls 35 that extend longitudinally between the first and second ends 22, 24 of the first member 14. In an alternate embodiment, the first channels 34 and first channel sidewalls 35 extend longitudinally between the first and second sides 26, 28 of the first member 14. The channel sidewalls 35 each have a rounded apex, as illustrated in FIGS. 2-3A. All of the first channels 34 have the same dimensions, and are evenly distributed across the first inner surface 30, as illustrated in FIGS. 2-4. In alternate embodiment(s), the first channels 34 may have different dimensions from each other and/or an uneven spacing/distribution across the first inner surface 30.

In alternate embodiment(s), the first channels 34 and sidewalls 35 may extend in different directions in relation to the first and second ends 22, 24 of the first member 14 and may be defined by sidewalls of different dimensions or shape.

In other alternate embodiment(s), the first inner surface 30 may not include a plurality of channels, and/or may include a plurality of protrusions, recesses, holes, or openings.

In still other alternate embodiments(s), the first inner surface 30 may include one or more structural features that are not channels or channel walls, through which and/or around which cryopreservation media may flow. Such structural features may include, but are not limited to, one or more elements formed as part of the first member 14 and/or the first inner surface 30, such as one or more grid patterns, one or more segments, one or more squares, or one or more dots. Such elements may be formed as part of a larger pattern/design on the first inner surface 30.

Figure 5:
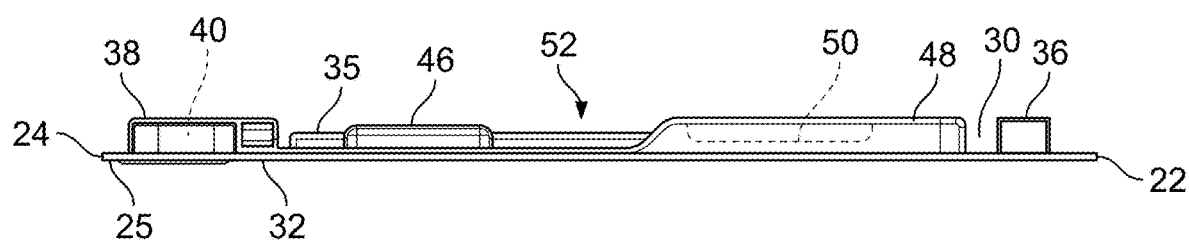
FIG. 5 is a right side elevational view of the first member of the tissue graft retainer of FIG. 2.

With continued reference to FIGS. 3-5, the first end 22 of the first member 14 includes a first end protrusion 36 that extends upwardly from the first inner surface 30. The second end 24 includes a second end raised area 38 that extends upwardly from the first inner surface 30, and defines a second end recess 40 (i.e., a groove or indentation) therein. The first end protrusion 36 and second end recess 40 constitute first engagement means of the first member 14 and are configured to removably engage similar, complimentary structures included on the second member 16, as will be described further below.

In an embodiment, the first end 22 also includes an additional (i.e., supplemental) first end protrusion 42 that extends upwardly from the first inner surface 30, and the second end raised area 38 of the second end 24 also defines an additional (i.e., supplemental) second end recess 44. The additional first end protrusion 42 and additional second end recess 44 are both positioned closer to the first channels 34 and first channel sidewalls 35 than the first end protrusion 36 and second end 40 recess, respectively. The additional first end protrusion 42 and additional second end recess 44 are configured to removably engage similar, complimentary structures included on the second member 16, as will be described further below.

The first side 26 of the first member 14 includes a first side protrusion 46 that extends upwardly from the first inner surface 30. The first side 26 also includes a first side raised area 48 that extends upwardly from the first inner surface 30 and defines a first side recess 50 (i.e., a groove or indentation) therein. The first side protrusion 46 is positioned proximate the second end 24, while the first side raised area 48 and first side recess 50 are positioned proximate the first end 22. The first side protrusion 46 and first side recess 50 are configured to removably engage similar, complimentary structures included on the second member 16, as will be described further below. The first engagement means of the first member 14 also includes the first side protrusion 46 and first side recess 50.

The first side protrusion 46 and first side raised area 48 cooperate to define a first side inlet 52 between them (see FIGS. 2-5). The first side inlet 52 is in fluid communication with the first channels 34, and facilitates the flow of cryopreservation media into the retainer 12 and to the tissue graft 18 and the suspension of the tissue graft 18 therein, which protects the viable cells of the tissue graft 18 throughout its shelf life, as will be described further below.

Referring to FIGS. 2-4, the second side 28 of the first member 14 includes similar structures as those of the first side 26. More particularly, the second side 28 includes a second side protrusion 54 that extends upwardly from the first inner surface 30. The second side 28 also includes a second side raised area 56 that extends upwardly from the first inner surface 30 and defines a second side recess 58 (i.e., a groove or indentation) therein. The second side protrusion 54 is positioned proximate the second end 24, while the second side raised area 56 and second side recess 58 are positioned proximate the first end 22. The second side protrusion 54 and second side recess 58 are configured to removably engage similar, complimentary structures included on the second member 16, as will be described further below. The first engagement means of the first member 14 also includes the second side protrusion 54 and second side recess 58.

The second side protrusion 54 and second side raised area 56 cooperate to define a second side inlet 60 between them (see FIGS. 2-5). Like the first side inlet 52, the second side inlet 60 is in fluid communication with the first channels 34, and facilitates the flow of cryopreservation media into the retainer 12 and to the tissue graft 18 and the suspension of the tissue graft 18 therein, which protects the viable cells of the tissue graft 18 throughout its shelf life, as will be described further below.

In the embodiment illustrated herein, the second member 16 and the first member 14 are identical (i.e., having the same structural features, dimensions, configurations and shapes as one another). The construction and operation of the second member 16 is described below.

Figure 6:
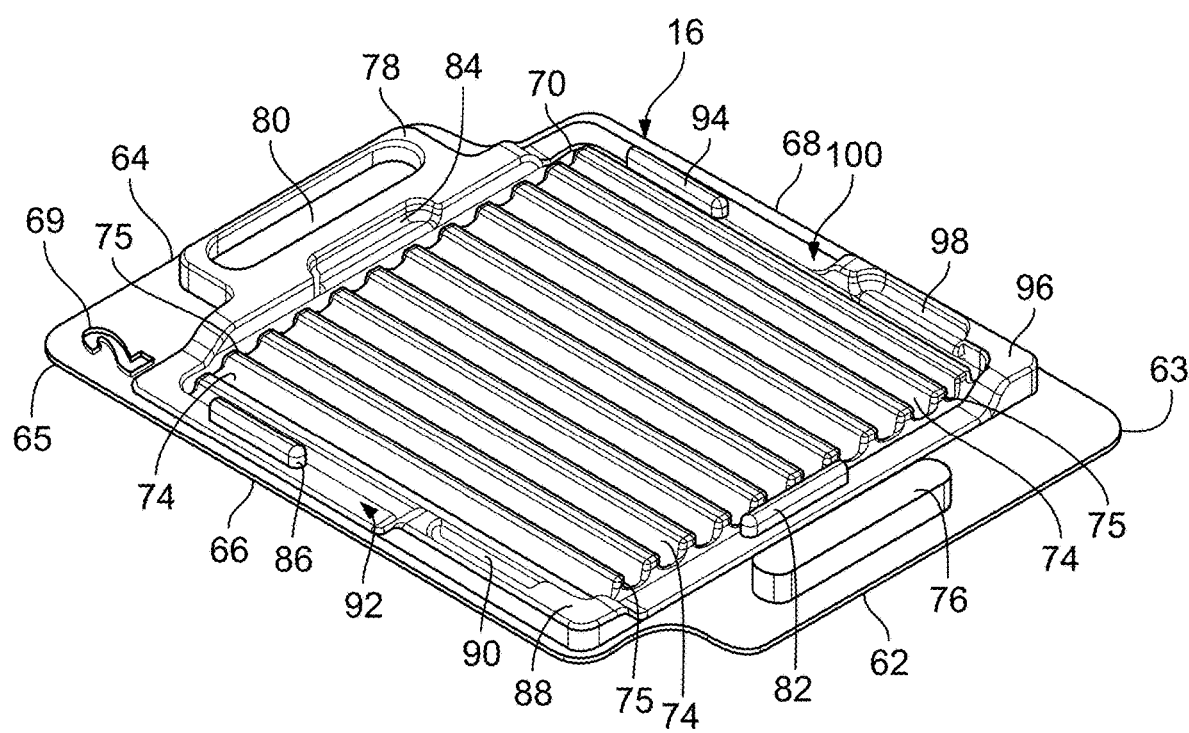
FIG. 6 is a perspective view of a second member of the tissue graft retainer of FIG. 2.

With reference to FIGS. 2 and 6, the second member 16 of the retainer 12 is substantially planar, and includes a third end 62 having a third corner tab 63, an opposed fourth end 64 having a fourth corner tab 65, and opposed third and fourth sides 66, 68 extending between the third and fourth ends 62, 64. In an embodiment, the third corner tab 63, fourth corner tab 65 and all other corners and edges of the second member 16 are rounded so as to avoid puncturing the pouches in which the retainer 12 is contained. Such pouches are described below.

In an embodiment, the fourth corner 65 includes second indicia 69, for purposes of correctly aligning the second member 16 with the first member 14 when assembling the retainer 12. The second indicia 69 may be an alphanumeric symbol (e.g., the numeral 2, as shown in FIG. 6) or other symbol that can be readily identified during packaging of the tissue graft 18. The second indicia 69 is preferably identical to the first indicia 29 on the first member 14, so as to simplify the packaging process. In alternate embodiments, the first indicia 29 and second indicia 69 are different, so as to allow the end user to distinguish one side of the tissue graft 18 from the other.

Figure 12:
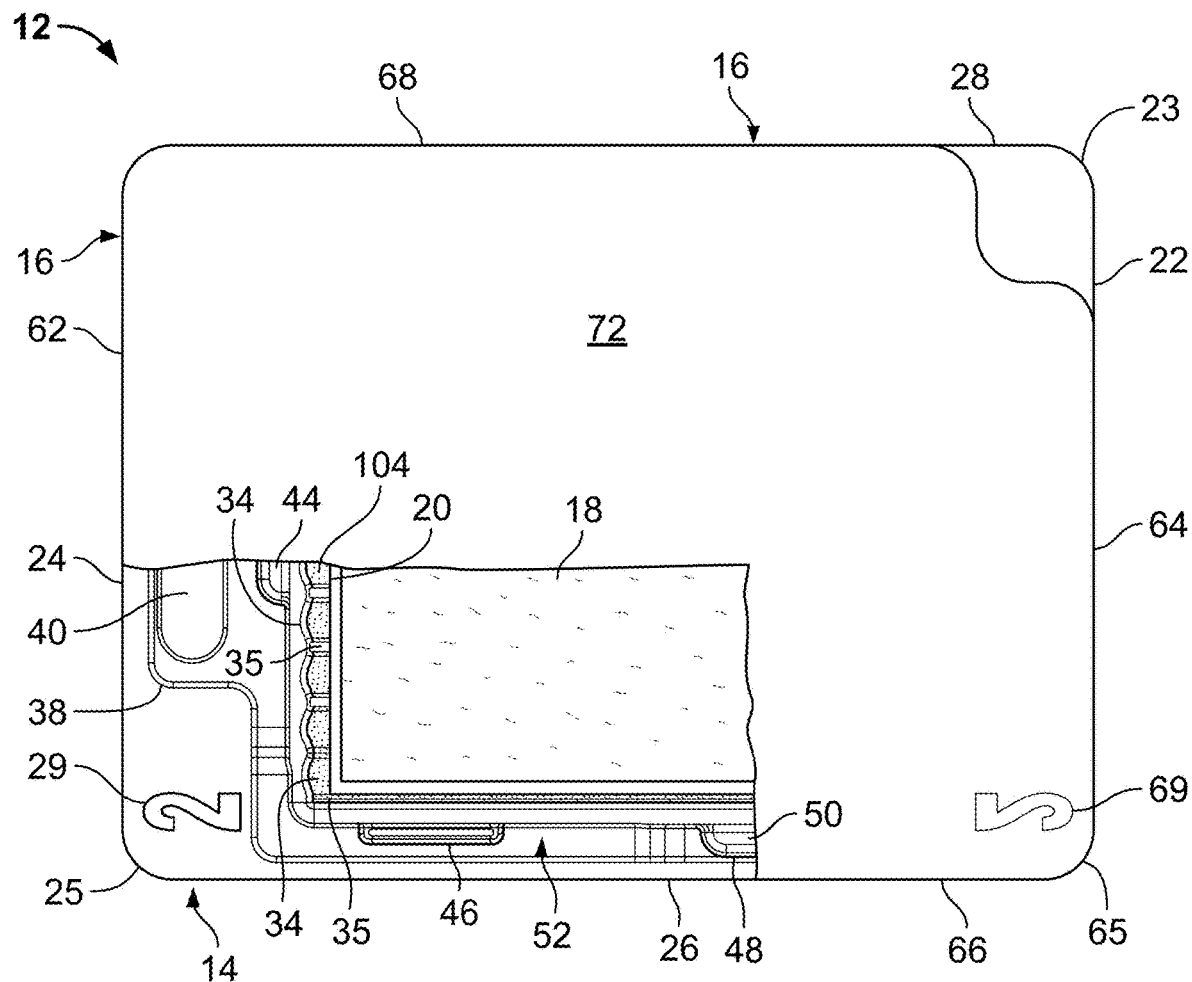
FIG. 12 is top plan view of the assembled tissue graft retainer of FIG. 7, with a portion of the second member broken away to show the tissue graft, backing and cryopreservation media therein.

The second member 16 further includes a second inner surface 70 that is positioned proximate the tissue graft 18 upon assembly of the retainer 12 of the packaging system 10, and a second outer surface 72 that is a positioned distal the tissue graft 18 upon assembly of the retainer 12 (see FIGS. 2, 6 and 12). The second inner surface 70 of the second member 16 includes a second plurality of channels 74 that extend longitudinally between the third and fourth ends 62, 64 of the second member 16. The second channels 74 are defined by a second plurality of channel sidewalls 75 that extend longitudinally between the third and fourth ends 62, 64 of the second member 16. In an alternate embodiment, the second channels 74 and second channel sidewalls 75 extend longitudinally between the first and second sides 66, 68 of the second member 16. The channel sidewalls 75 each have a rounded apex, as illustrated in FIG. 6. All of the second channels 74 have the same dimensions, and are evenly distributed across the second inner surface 70, as illustrated in FIG. 6. In alternate embodiments, the second channels 74 may have different dimensions from each other and/or an uneven spacing/distribution across the second inner surface 70.

In alternate embodiment(s), the second channels 74 and sidewalls 75 may extend in different directions in relation to the third and fourth ends 62, 64 of the second member 16 and may be defined by sidewalls of different dimensions or shape.

In other alternate embodiment(s), the second inner surface 70 may not include a plurality of channels, and/or may include a plurality of protrusions, recesses, holes, or openings.

In still other alternate embodiments(s), the second inner surface 70 may include one or more structural features that are not channels or channel walls, through which and/or around which cryopreservation media may flow. Such structural features may include, but are not limited to, one or more elements formed as part of the second member 16 and/or the second inner surface 70, such as one or more grid patterns, one or more segments, one or more squares, or one or more dots. Such elements may be formed as part of a larger pattern/design on the second inner surface 70.

The second channels 74 also have the same dimensions, spacing/distribution and orientation (i.e., extending longitudinally along the same axis and direction) as the first channels 34. In an alternate embodiment, the second channels 74 may have one or more different dimensions, distribution and/or orientation from the first channels 34. For example, in an embodiment, the second channels 74 extend longitudinally between the third and fourth sides 66, 68 of the second member 16, and the first channels 34 extend longitudinally between the first and second ends 22, 24 of the first member 14, such that the second channels 74 are oriented perpendicularly to the first channels 34 upon assembly of the retainer 12.

Figure 9:
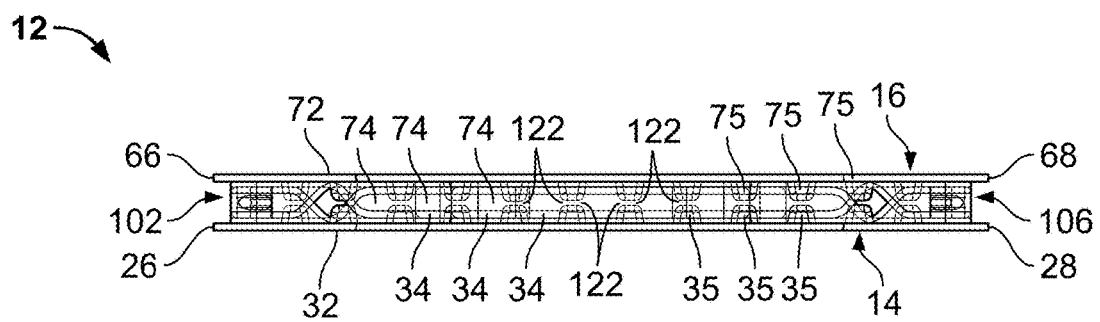
FIG. 9 is a sectional view, taken through line 9-9 in FIG. 7, of the assembled tissue graft retainer of FIG. 7.
Figure 10:
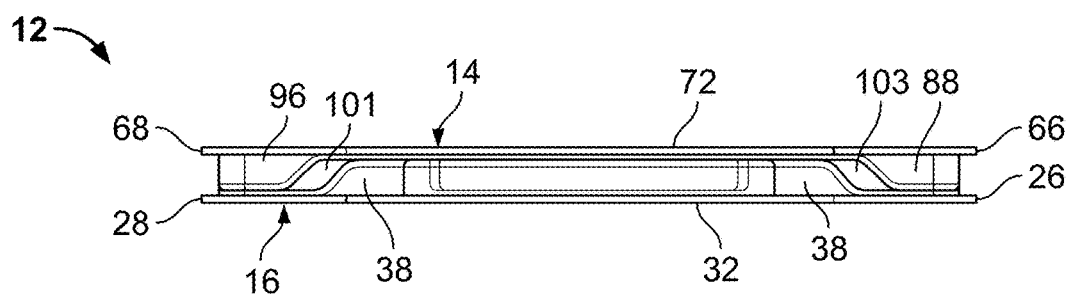
FIG. 10 is a rear end elevational view of the assembled tissue graft retainer of FIG. 7.
Figure 11:
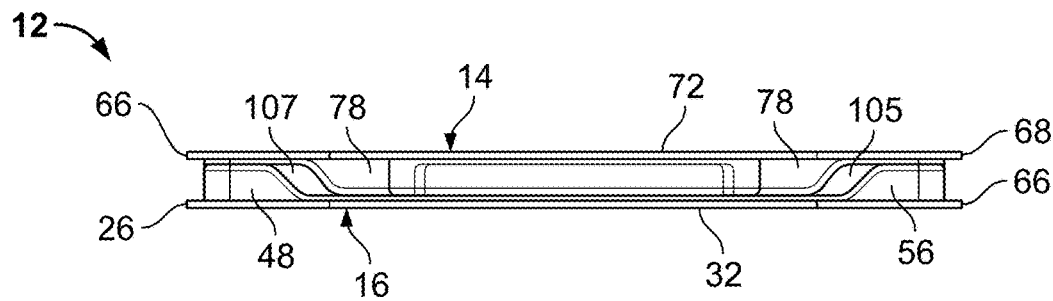
FIG. 11 is a front end elevational view of the assembled tissue graft retainer of FIG. 7.

Upon assembly of the retainer 12, the first channels 34 and second channels 74 do not mate. More particularly, the first channel sidewalls 35 do not come into contact with the second channel sidewalls 75 when the first and second members 14, 16 are connected to each other via their respective first and second engagement means (see FIGS. 7A and 9). This arrangement facilitates the creation of a continuous interior space (i.e., a gap) 122 between the first and second members 14, 16 in which the tissue graft 18 is maintained, as illustrated in FIG. 9 and further described below.

With continued reference to FIG. 6, the third end 62 of the second member 16 includes a third end protrusion 76 that extends upwardly from the second inner surface 70. The fourth end 64 includes a fourth end raised area 78 that extends upwardly from the second inner surface 70, and defines a fourth end recess 80 (i.e., a groove or indentation) therein. The third end protrusion 76 and fourth end recess 80 constitute second engagement means of the second member 16. The third end protrusion 76 is configured to insertably and removably engage the second end recess 40 of the first member 14 (i.e., upon assembly of the retainer 12), while the first end protrusion 36 of the first member 14 is configured to insertably and removably engage the fourth end recess 80, as further described below. For example, the third end protrusion 76 may be oval-shaped and the second end recess 40 may be oval-shaped but slightly smaller than the third end protrusion 76 so as to facilitate an interference fit therewith, and the first end protrusion 36 and fourth end recess 80 may be similarly shaped and sized so as to also facilitate an interference fit therewith. For example, the third end protrusion 76 may be oval-shaped and the second end recess 40 may be oval-shaped but slightly smaller than the third end protrusion 76 so as to facilitate an interference fit therewith, and the first end protrusion 36 and fourth end recess 80 may be similarly shaped and sized so as to also facilitate an interference fit therewith. In an alternate embodiment, the third end protrusion 76 has the same dimensions as the second end recess 40, so as to facilitate a press-fit therebetween, and the first end protrusion 36 has the same dimensions as fourth end recess 80, so as to facilitate a press-fit therebetween.

In an embodiment, the third end 62 also includes an additional (i.e., supplemental) third end protrusion 82 that extends upwardly from the second inner surface 70, and the fourth end raised area 78 of the fourth end 64 also defines an additional (i.e., supplemental) fourth end recess 84. The additional third end protrusion 82 and additional fourth end recess 84 are both positioned closer to the second channels 74 and second channel sidewalls 75 than the third end protrusion 76 and fourth end 80 recess, respectively.

The additional third end protrusion 82 is configured to insertably and removably engage the additional second end recess 44 of the first member 14 (i.e., upon assembly of the retainer 12), and functions to facilitate the correct alignment of the first and second members 14, 16. Similarly, the additional first end protrusion 42 of the first member 14 is configured to insertably and removably engage the additional fourth end recess 84, and also functions to facilitate the correct alignment of the first and second members 14, 16 upon assembly of the retainer 12. The additional first end protrusion 42, additional second end recess 44, additional third end protrusion 82 and additional fourth end recess 84 thereby function as alignment guides for the tissue graft processor/packager, as further discussed below.

The third side 66 of the second member 16 includes a third side protrusion 86 that extends upwardly from the second inner surface 70. The third side 66 also includes a third side raised area 88 that extends upwardly from the second inner surface 70 and defines a second side recess 90 (i.e., a groove or indentation) therein. The third side protrusion 86 is positioned proximate the fourth end 64, while the third side raised area 88 and third side recess 90 are positioned proximate the third end 62. The second engagement means of the second member 16 also includes the third side protrusion 86 and third side recess 90.

Figure 7:
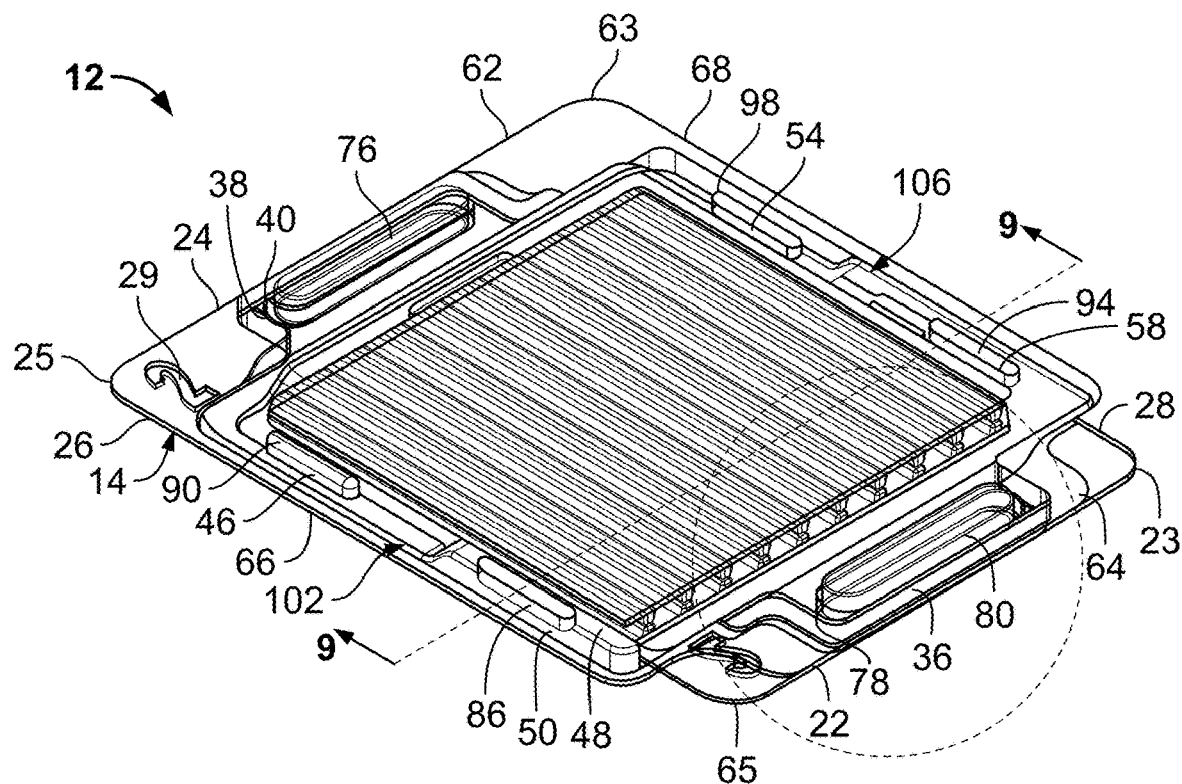
FIG. 7 is a perspective view of the tissue graft retainer of FIG. 2, showing the first and second members assembled together.
Figure 7A:
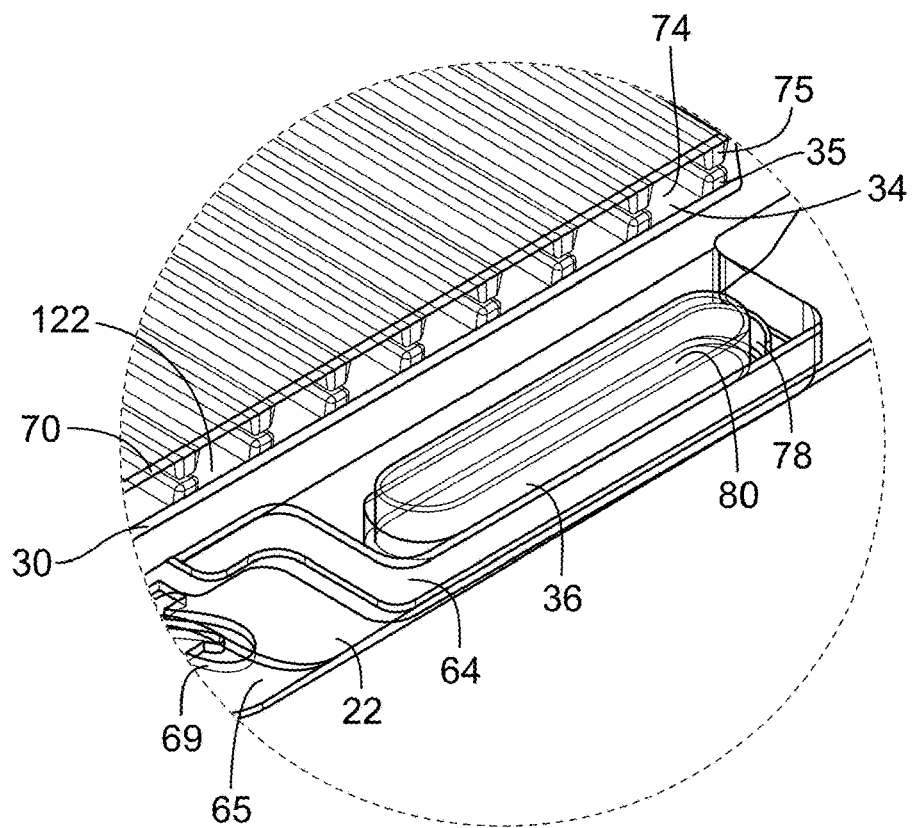
FIG. 7A is an enlarged perspective view of a portion of the assembled tissue graft retainer of FIG. 7.
Figure 8:
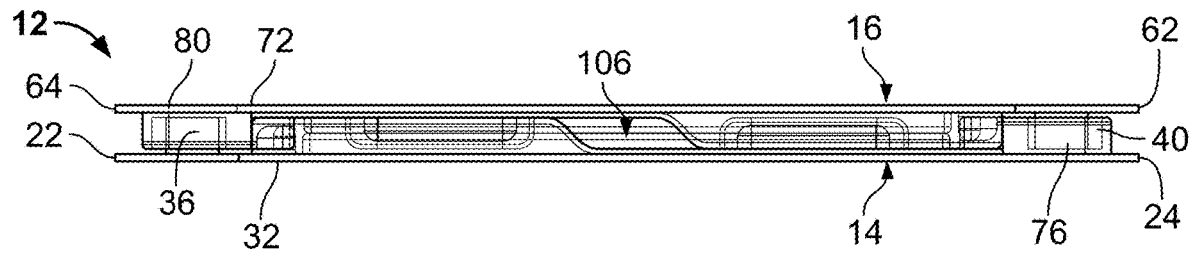
FIG. 8 is a left side elevational view of the assembled tissue graft retainer of FIG. 7.

As illustrated in FIG. 7, the third side protrusion 86 is configured to insertably and removably engage the first side recess 50 of the first member 14 (i.e., upon assembly of the retainer 12), while the first side protrusion 46 of the first member 14 is configured to insertably and removably engage the third side recess 90 of the second member 16.

The third side protrusion 86 and third side raised area 88 cooperate to define a third side inlet 92 between them (see FIG. 6). The third side inlet 92 is in fluid communication with the second channels 74, and facilitates the flow of cryopreservation media into the retainer 12 and to the tissue graft 18 and the suspension of the tissue graft 18 therein, which protects the viable cells of the tissue graft 18 throughout its shelf life, as will be described further below.

The fourth side 68 of the second member 16 includes similar structures as those of the third side 66. More particularly, the fourth side 68 of the second member 16 includes a fourth side protrusion 94 that extends upwardly from the second inner surface 70. The fourth side 68 also includes a fourth side raised area 96 that extends upwardly from the second inner surface 70 and defines a fourth side recess 98 (i.e., a groove or indentation) therein. The fourth side protrusion 94 is positioned proximate the fourth end 64, while the fourth side raised area 96 and fourth side recess 98 are positioned proximate the third end 62. The second engagement means of the second member 16 also includes the fourth side protrusion 94 and fourth side recess 98.

As illustrated in FIG. 7, the fourth side protrusion 94 is configured to insertably and removably engage the second side recess 58 of the first member 14 (i.e., upon assembly of the retainer 12), while the second side protrusion 54 of the first member 14 is configured to insertably and removably engage the fourth side recess 98 of the second member 16.

The fourth side protrusion 94 and fourth side raised area 96 cooperate to define a fourth side inlet 100 between them (see FIG. 6). Like the third side inlet 92, the fourth side inlet 100 is in fluid communication with the second channels 74, and facilitates the flow of cryopreservation media into the retainer 12 and to the tissue graft 18 and the suspension of the tissue graft 18 therein, which protects the viable cells of the tissue graft 18 throughout its shelf life, as will be described further below.

The first and second members 14, 16 of the retainer 12 may be formed (e.g., via thermoforming, or any suitable alternate manufacturing method) from any biologically inert material that can operably withstand cryopreservation temperatures (e.g., <0° C. to −196° C.). Such materials include, but are not limited to, polyethylene terephthalate glycol-modified (PETG), high-impact polystyrene (HIPS), polystyrene, polypropylene, or any plastic derivative of the foregoing materials. In an embodiment, the material is transparent or translucent, such that the tissue graft 18 may be visible through the retainer 12 during packaging, handling and surgery (or use in other, non-surgical medical procedures). In alternate embodiments, the first and/or second members 14, 16 are made of an opaque material, or a semi-opaque material. The first and/or second members 14, 16 can be made of the same material or different materials.

In an embodiment, the first and second members 14, 16 of the retainer 12 are identical (i.e., having the same structural features, dimensions, configurations and shapes as one another), which simplifies both the manufacturing and operation of the retainer 12. In an embodiment, the size of the first and second members 14, 16 may range from 1 cm×1 cm to 15 cm×15 cm. Such sizes include, but are not limited to, a 1 cm diameter, a 3 cm×3 cm square, a 5 cm×5 cm square, a 10 cm×10 cm square, and a 7.5 cm×15 cm rectangle. In alternate embodiments, the first member 14 may have a different size, shape and/or configuration than the second member 16.

For illustrative purposes, FIGS. 7-11 show the retainer 12 as assembled (i.e., with the first and second members 14, 16 connected to each other by way of their respective first and second engagement means), but without containing the tissue graft 18 (or its backing 20) within. FIG. 12 shows a portion of the second member 16 of the retainer 12 broken away to reveal the tissue graft 18, backing 20 and cryopreservation media 104 therein. Reference to the foregoing figures, and FIGS. 1 and 2, will be made throughout the following discussion of the operation and assembly of the retainer 12 and other components of the tissue packaging system 10 of the present invention, and the associated tissue graft 18 and backing 20, where applicable.

While the retainer 12 and tissue packaging system 10 of the present invention are described below in connection with a cryopreserved viable tissue graft 18 having a sheet-like configuration (i.e., a planar, single-layer graft), it is understood that the retainer 12 and tissue packaging system 10 may also be used for other viable tissue grafts and tissue-engineered scaffolds with seeded cells that also require cryopreservative media, as well as sheet-like decellularized tissue grafts, and non-sheet-shaped tissue grafts, such as three-dimensional tissue grafts. The retainer 12 may also be used with non-cryopreserved tissue grafts or tissue-engineered scaffolds, such as those stored at refrigerated temperature or room (i.e., ambient) temperature. If desired, an alternate solution may be substituted for the cryopreservation solution, and such alternate solution may optionally not have any cryopreservation capabilities. Alternatively, the solution may be omitted from the retainer 12 completely. Tissue-engineered scaffolds as described above for use with the retainer 12 can be either naturally-occurring, naturally-derived, synthetic, or a combination thereof. Further, the retainer 12 and tissue packaging system 10 may alternatively be used with multiple (i.e., two or more) tissue grafts.

Donor tissues are processed for preparation of a tissue graft 18 that may be used as an allograft in various surgical and other medical procedures (e.g., opthalmological, genitourinary, wound healing, burn care, surgical anti-adhesion, dental, orthopaedic, plastic and reconstructive surgery, etc.). Generally, the donor tissue is processed (e.g., removed from any adjacent tissue(s), cleaned to remove blood and blood clots and soaked in an antibiotic solution) and cut into a number of tissue grafts 18 having a sheet (i.e., single layer) configuration. Such tissue grafts 18 can be of any dimension, as discussed in the Examples herein.

The finished tissue graft 18 is then placed into the retainer 12, cryopreserved (optionally via controlled rate freezing (e.g., 1° C./min.) and maintained in cryopreservation media until it is thawed, shortly before its use in surgery (or other medical applications), as described further below. The tissue graft 18 may optionally be supported by, and packaged with, a backing 20 (see FIGS. 2 and 12) that is maintained in contact with (i.e., removeably secured to) the tissue graft 18. In an embodiment, the backing 20 is maintained in contact with the tissue graft 18 via surface tension between them. In an embodiment, the two sides of the backing 20 have different surfaces, namely, a meshed side and non-meshed side, and the tissue graft 18 is placed on the meshed side to provide surface tension between the backing 20 and the tissue graft 18, and thereby secure the tissue graft 18 to the backing 30. In an embodiment, the backing 20 is labeled to indicate which side of the tissue graft 18 is face-down or face-up (i.e., in the event that a first side of the tissue graft 18 is different from a second side thereof), which enables a healthcare provider (e.g., a surgeon) to easily identify each side. The backing 20 may alternatively be directly applied to the first or second side of the tissue graft 18 for such identification purposes. In other embodiments, the backing 20 can include other sidedness indicators such as texture, marking and/or color.

The backing 20 is maintained in contact with (i.e., removeably secured to) the tissue graft 18 (e.g., via surface tension) so as to enable a healthcare provider to remove the backing 20 easily (e.g., after the tissue graft 18 is applied to a wound), as also described below.

With continued reference to FIGS. 2 and 12, the tissue graft 18, and the optional backing 20, is placed on the first inner surface 30 of the first member 14 of the retainer 12, so as to engage the first channel sidewalls 35 thereof and thereby be in contact with the first channels 34. The tissue graft 18, and the backing 20, may alternatively be placed on the second inner surface 70 of the second member 16 of the retainer 12, so as to engage the second channel sidewalls 75 thereof and thereby be in contact with the second channels 74.

As illustrated in FIG. 12, and also in FIG. 2, the first and second members 14, 16 of the retainer 12 have a larger surface area than that of the tissue graft 18 and its backing 20. In an embodiment, the backing 20 itself has a larger surface area than that of the tissue graft 18, such that at least one edge of the backing 20 does not come into contact with the tissue graft 18, and therefore facilitates the separation of the backing 20 from the tissue graft 18 by the healthcare provider.

In other embodiments, the first and/or second members 14, 16 of the retainer 12 have a surface area that is the same size as or smaller than that of the tissue graft 18 and its backing 20. In yet other embodiments, the backing 20 has a surface area that is the same size as or smaller than that of the tissue graft 18.

The first and second members 14, 16 are then secured to one another via their respective first and second engagement means (by, i.e., a tissue graft processor/packager), with the tissue graft 18, and the optional backing 20, being enclosed within the continuous interior space 122 between the first and second members 14, 16. More particularly, in the embodiment illustrated in FIGS. 7-12, the retainer 12 is assembled by at least the steps of (1) removably inserting (i.e., snapping) the third end protrusion 76 of the second member 16 into the second end recess 40 of the first member 14, and (2) removably inserting (i.e., snapping) the first end protrusion 36 of the first member 14 into the fourth end recess 80 of the second member 16. The first and second members 14, 16 are further secured to one another by the steps of (3) removably inserting (i.e., snapping) the third side protrusion 86 of the second member 16 into the first side recess 50 of the first member 14; (4) removably inserting (i.e., snapping) the first side protrusion 46 of the first member 14 into the third side recess 90 of the second member 16; (5) removably inserting (i.e., snapping) the fourth side protrusion 94 of the second member 16 into the second side recess 58 of the first member 14; and (6) removably inserting (i.e., snapping) the second side protrusion 54 of the first member 14 into the fourth side recess 98 of the second member 16. In alternate embodiments, fewer than all of these steps (i.e., fewer than all of the foregoing protrusions and recesses) may be used to secure the first and second members 14, 16 of the retainer 12 together.

The first and second members 14, 16 are configured and manufactured such that when secured to one another, a minimum retention force is required to maintain the interconnection of the first and second members 14, 16, with the tissue graft 18 between them. In an embodiment, the minimum retention force is 18 Newtons (18 N).

In alternate embodiments, the aforementioned minimum retention force may be less than or greater than 18 N. For example, the minimum retention force may range from 5 N to 100 N, and may be, without limitation, 8 N, 9 N, 10 N, 20 N or 30 N. In another alternate embodiment, there is no minimum retention force required to maintain the interconnection of the first and second members 14, 16 (i.e., the "minimum" retention force is 0 N).

The first and second indicia 29, 69 on the corner tabs 25, 65 of the first and second members 14, 16, respectively, may be used by the tissue graft processor/packager to align the first and second members 14, 16 according to the proper orientation upon assembly. As illustrated in FIG. 7, the first and second indicia 29, 69 are aligned on the same side of the assembled retainer 12 (i.e., the side corresponding to the first side 26 of the first member 14 and the aligned, adjacent third side 66 of the second member 16). The first and second indicia 29, 69 thereby facilitate efficient and accurate assembly of the retainer 12.

As indicated above, the additional third end protrusion 82 insertably and removably engages the additional second end recess 44 to facilitate the correct alignment of the first and second members 14, 16 upon assembly of the retainer 12 (i.e., by the tissue graft processor/packager). Similarly, the additional first end protrusion 42 insertably and removably engages the additional fourth end recess 84 to facilitate the correct alignment of the first and second members 14, 16 upon assembly of the retainer 12. In assembling the retainer 12, the tissue graft processor/packager would removably insert (i.e., snap) the additional third end protrusion 82 of the second member 16 into the additional second end recess 44 of the first member 14, and removably insert (i.e., snap) the additional first end protrusion 42 of the first member 14 into the additional fourth end recess 84 of the second member 16.

Upon assembly of the first and second members 14, 16 of the retainer 12, the first side inlet 52 and third side inlet 92 cooperate to form a first side passageway 102 through which cryopreservation media 104 flows into and out of the assembled retainer 12 (see FIGS. 7 and 9). Likewise, the second side inlet 60 and fourth side inlet 100 cooperate upon assembly of the first and second members 14, 16 to form a second side passageway 106 through which cryopreservation media 104 flows into and out of the assembled retainer 12 (see FIGS. 7-9).

Upon assembly of the retainer 12, first and second members 14, 16 also cooperate to form end passageways through which cryopreservation media 104 flows into and out of the assembled retainer 12. More particularly, the fourth side raised area 96 cooperates with the second end raised area 38 to form a first end passageway 101 between them, and the third side raised area 88 cooperates with the second end raised area 38 to form a second end passageway 103 between them (see FIG. 10). In addition, the second side raised area 56 cooperates with the third end raised area 78 to form a third end passageway 105 between them, and the first side raised area 48 cooperates with the third end raised area 78 to form a fourth end passageway 107 between them (see FIG. 11). The first, second, third and fourth end passageways 101, 103, 105, 107 are in fluid communication with said first and second pluralities of channels 34, 74.

The respective components of the first and second members 14, 16 (e.g., the first and second channel sidewalls 35, 75 and/or first and second inner surfaces 30, 70) are configured such that they minimally contact the tissue graft 18 between them when the first and second members 14, 16 are secured to one another.

In an embodiment, such minimal contact may constitute no contact (i.e., touching) between the respective components of the first and/or second members 14, 16 and the tissue graft 18. In another embodiment, such minimal contact may constitute light contact between the respective components of the first and/or second members 14, 16 and the tissue graft 18, such that the components do not exert an amount of pressure on the tissue graft 18 sufficient to compromise and/or damage the viability of the tissue thereof (e.g., by crushing, pinching or compressing the tissue graft 18). More particularly, the tissue graft 18 is maintained within the continuous interior space 122, which provides sufficient space (i.e., clearance) between the first channels 34 of the first member 14 and the second channels 74 of the second member 16, so as to facilitate the suspension of the tissue graft 18 in the cryopreservation media 104, and minimal contact between the tissue graft 18 and the first and second channel sidewalls 35, 75 and/or first and second inner surfaces 30, 70. In an embodiment, the clearance between the apexes of the first channel walls 35 and the apexes of the second channel walls is at least slightly greater than the average thickness of the tissue graft 18 (and, if present, the backing 20), such that the continuous interior space 122 has a height that is greater than the height (i.e., thickness) of the tissue graft 18, or the combined height (i.e., thickness) of the tissue graft 18 and backing 20. In another embodiment, the continuous interior space 122 has a height that is approximately the same height (i.e., thickness) of the tissue graft 18, or the combined height (i.e., thickness) of the tissue graft 18 and backing 20.

In an embodiment, the first and second channel sidewalls 35, 75 are also not in constant contact with the tissue graft 18 (i.e., the tissue graft 18 moves within the continuous interior space 122, suspended in the cryopreservation media 104, so that the tissue graft 18 may, at various times, be supported by the first inner surface 30 and the first channel sidewalls 35 thereof, or be supported by the second inner surface 70 and the second channel sidewalls 75 thereof, or float in the cryopreservation media 104 between the first and second inner surfaces 30, 70). The first and second channel sidewalls 35, 75 therefore do not block/impede the cryopreservation media 104 from reaching any portion of the tissue graft 18, which could otherwise adversely affect the viability of the tissue graft 18.

While the tissue graft 18 may move within the retainer 12 (i.e., within the continuous interior space 122, while suspended in the cryopreservation media 104), the various complimentarily-engaged protrusions and recesses of the interconnected first and second members 14, 16 (i.e., the first and second engagement means) prevent egress of the tissue graft 18 outside of the retainer 12. In the meantime, the first and second side passageways 102, 106 and first, second, third and fourth end passageways 101, 103, 105, 107 are dimensioned such that the cryopreservation media 104 may freely flow into the retainer 12 to suspend the tissue graft 18 therein, but not large enough to permit passage of the tissue graft 18 therethrough.

Once the tissue graft 18 has been secured within the retainer 12, the retainer 18 is placed into an inner pouch 108, as illustrated in FIG. 1. The inner pouch 108 is then filled with an amount (i.e., volume) of cryopreservation media 104. In an embodiment, 20 ml of cryopreservation media 104 is used, although other volumes are contemplated. In an embodiment, the cryopreservation media 104 is a solution containing a cryoprotectant known in the art, such as dimethyl sulfoxide (DMSO). Other types of cryoprotectant may alternatively be used.

The inner pouch 108 is then sealed, containing the retainer 12, tissue graft 18 and cryopreservation media 104 therein. As indicated above, the cryopreservation media 104 flows freely from the inner pouch 108 (outside of the retainer 12) into the retainer 12 through the first and second side passageways 102, 106 thereof and the first, second, third and fourth end passageways 101, 103, 105, 107 thereof, and through its first and second channels 34, 74, to immerse the tissue graft 18 therein, and thereby preserve the viability of the cells of the tissue graft 18 throughout its shelf life.

One or more labels 110, 112 may be applied to the outside of the sealed inner pouch 108. Such labels 110, 112 may convey information about the tissue graft 18, including its orientation (e.g., which side of the graft is face-down on the backing 20 or face-up) and donor and/or lot numbers (e.g., via alphanumeric and/or bar code). The sealed inner pouch 108 is then placed within an outer pouch 114, which is then sealed. A label 116 may be applied to the outside of the sealed outer pouch 114. The label 116 may also convey information about the tissue graft 18 (e.g., its donor and/or lot numbers (e.g., via alphanumeric and/or bar code)).

The outer pouch 114 is then loaded into controlled rate freezer (e.g., a CryoMed™ controlled rate freezer, Thermo Fischer Scientific, Waltham, Mass.), by which the tissue graft 18 is cryopreserved. Once the desired cryopreservation temperature has been attained, the outer pouch 114 is removed from the controlled rate freezer and stored in a freezer under approved storage conditions (e.g., −80° C.). Cryopreservation temperatures may range from <0° C. to −196° C., and may include, by way of example only, −20° C., −40° C., −70° C., −80° C., and −100° C.

Prior to supplying the cryopreserved tissue graft 18 to a hospital or other end user, the outer pouch 114 containing same is placed in a carton 118, which may include a label 120 with information regarding the cryopreserved tissue graft 18 (e.g., its donor and/or lot numbers (e.g., via alphanumeric and/or bar code)) and/or the use thereof. The carton 118 may be made from any suitable material (e.g., corrugated cardboard, paperboard, etc.). In an embodiment, the carton 118 is laminated so that it can better withstand freezing temperatures/conditions.

A package insert containing instructions for use and other information (not shown) may also be placed inside the carton 118. Such instructions for use may include how to thaw and rinse the cryopreserved tissue graft 18 prior to surgery (or other medical procedure performed by a healthcare provider), a method that is facilitated by the design of the retainer 12, as further described below.

In an embodiment, the following graft defrosting and preparation protocol is followed prior to a surgery, or other medical procedure performed by a healthcare provider, involving the implantation or application of the tissue graft 18. The carton 118 containing the outer pouch 114, inner pouch 108, retainer 12 and tissue graft 18 is removed from the hospital (or surgical center or other end user) freezer and delivered to the surgical suite (i.e., operating room or other surgical area), or applicable medical treatment area. The outer pouch 114 is removed from the carton 118 and opened, enabling a healthcare provider to retrieve the sealed inner pouch 108 and pass it into a sterile field within the surgical suite. The inner pouch 108 contains the tissue graft 18, the backing 20, and retainer 12, as well as the cryopreservation media 104. In an embodiment, the cryopreservation media 104 is a first color (e.g., yellow).

The sealed inner pouch 108 is placed into a first basin containing enough thawing solution (e.g., saline or other appropriate biocompatible liquid) to completely submerge the inner pouch 108 therein, or enough thawing solution to at least contact a surface of the inner pouch 108. Placement of the inner pouch 108 in the thawing solution facilitates the thawing of the tissue graft 18 still sealed therein. The thawing solution may be room temperature, or a higher temperature, such as 37° C., or any appropriate temperature up to and including 40° C.

The tissue graft 18 is completely thawed when no more ice is visible. In one embodiment, the cryopreservation media 104 turns a second color (e.g., red) to indicate that the tissue graft 18 is completely thawed. Alternatively, the cryopreservation media 104 may not undergo a change in color upon complete thawing of the tissue graft 18.

The inner pouch 108 is then removed from the first basin and opened, wherein the cryopreservation media 104 is discarded and the retainer 12 containing the tissue graft 18 is removed from the inner pouch 108 and placed into a second basin containing a rinse solution to remove residual cryopreservation media 104. In an embodiment, the rinse solution may constitute 5% dextrose in lactated ringer's solution, which maintains the cell viability of the tissue graft 18. Alternatively, the rinse solution may constitute physiological saline solution (i.e., 0.9% saline w/v). The retainer 12 is fully submerged in the rinse solution for at least 5 minutes, generally not more than one hour, and at most for four hours. The first and second side passageways 102, 106, and first, second, third and fourth end passageways 101, 103, 105, 107 of the retainer 12 facilitate the flow of residual cryopreservation media 104 out of the retainer 12, as well as the flow of the rinse solution into and out of the retainer 18, to more effectively rinse the tissue graft 18.

Once the residual cryopreservation media 104 has been rinsed from the tissue graft 18, it is ready for use. The retainer 12 is opened by disengaging the first engagement means (e.g., the first end protrusion 36, second end recess 40, first side protrusion 46, first side recess 50, second side protrusion 54, and/or second side recess 58) from the second engagement means (e.g., the third end protrusion 76, fourth end recess 80, third side protrusion 86, third side recess 90, fourth side protrusion 94 and/or fourth side recess 98) to separate the first and second members 14, 16 from each other.

The tissue graft 18 is then removed from the retainer 12 with its backing 20, and a healthcare provider may manipulate the tissue graft 18 based on which side the healthcare provider prefers to be placed downward to face a patient's body (e.g., to be in contact with a wound). As indicated in the embodiment disclosed above, the backing 20 may be directly applied to the first or second side of the tissue graft 18 for identifying that side (i.e., in the event that the first side of the tissue graft 18 is different from the second side). The opposing side of the tissue graft 18 is therefore exposed (i.e., not in contact with or covered by the backing 20). A healthcare provider can lift the tissue graft 18 off of the backing 20 with a forceps (e.g., starting by lifting a corner of the tissue graft 18) in order to expose the underlying side of the tissue graft 18 and place it facing downward on a wound. Alternatively, the healthcare provider can place the exposed side of the tissue graft 18 facing downward on the wound by leaving the tissue graft 18 on the backing 20 until after the tissue graft 18 is applied to the wound, and then carefully removing the backing 20 from opposite side of the tissue graft 18. The backing 20 is maintained on the tissue graft 18 (e.g., by surface tension) to enable its removal without disrupting the placement of the tissue graft 18 on the wound. The healthcare provider may, alternatively, not make any distinction or decision to orient a certain side of the tissue graft 18 downward.

Alternatively, the tissue graft 18 could be removed from the backing 20 and used in other wound care or medical applications other than those where it is layered down onto a wound bed. Such applications include, for example, balling, rolling or otherwise shaping the tissue graft 18 prior to placement onto a wound; cutting the tissue graft 18 into smaller pieces prior to placement onto a wound; "stuffing" the tissue graft 18 into a wound, etc. The tissue graft 18 could also be removed from the backing 20 and used in any non-wound care medical or surgical application, including, but not limited to, placement onto or within another allograft or non-allograft medical product prior to use; placement as a layer between human tissues during orthopaedic or general surgery procedures; use for replacement of a naturally-occurring membrane in the human body (e.g., tympanic membrane, pericardium, omentum, interstitial membranes, and other membranes or sheet-like structures), etc. The tissue graft 18 could also be removed from the backing 20 and used for in vitro diagnostic or research applications, including but not limited to, cell culture, tissue culture, microbiology, bioreactors, or other tissue engineering applications.

It will be understood that the embodiments described herein are merely exemplary and that a person of ordinary skill in the art may make many variations and modifications without departing from the spirit and scope of the invention. All such variations and modifications are intended to be included within the scope of the invention as defined in the appended claims. While not meant to be limiting, some of the possible variations and modifications are described below.

The retainer of the packaging system 10 of the present invention may be formed of two interconnected members rather than two separate members. Such a retainer may have a "clamshell" configuration, or otherwise have a hinge element between the interconnected members to facilitate the opening and closing thereof.

The first and second engagement means of the retainer could also include a "butterfly" closure. More particularly, the first engagement means may include two outer tabs positioned on an end or side of the first member of the retainer, and the second engagement means may include one middle tab positioned on a corresponding end or side of the second member of the retainer, wherein the middle tab is depressed, or snapped, between the two outer tabs to secure the tissue graft within the first and second members.

In other alternate embodiments, the first and second members 14, 16 of the retainer 12 may be secured together (i.e., on either side of the tissue graft) by external engagement means. Such external engagement means include, but are not limited to, one or more clamps, one or more retaining rings, one or more pieces of adhesive tape or labels affixed to both first and second members, one or more rubber bands, and/or the inner pouch 108 that is sized and shaped to have a cavity that is only slightly larger than the assembled retainer 12, such that the first and second members 14, 16 are secured to one another as a result of tightly fitting inside the cavity of the inner pouch 108.

In an alternate embodiment, a plurality of smaller tissue grafts, (e.g., particles or "mini sheets") may be packaged in the system of the present invention.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g., amounts, temperatures, etc.) but some experimental errors and deviations should be accounted for. Unless indicated otherwise, temperature is in degrees centigrade, force is measured in Newtons (N), and energy is measured in Joules (J).

Example 1—Assessment of the Ability to Contain the Tissue Graft

The ability of the retainer to contain the tissue graft may be assessed by measuring the minimum and maximum clearance between the assembled/closed retainer members within and around the perimeter and degree of parallelism, where the clearance must be greater than the smallest dimension of the tissue graft within the perimeter and the clearance around the perimeter must be less than the smallest dimension of the tissue graft to prevent the tissue graft from migrating to the outside of the retainer. For example, if the tissue graft is 2 cm×2 cm×50-200 µm, the clearance within the perimeter must be greater than 50 µm and the clearance around the perimeter must be less than 200 µm. The length of any negative space that may be present in the perimeter of the retainer may also be measured, where it is less than the greatest dimension of the tissue graft. For example, if the tissue graft is 2 cm×2 cm×50-200 µm, the negative space in the perimeter must be less than 2 cm. These dimensions and aspects may be measured using any device or instrument for measuring dimension including but not limited to, calipers, gauge blocks, a feeler gauge, a micrometer, or a comparator.

Example 2—Assessment of the Ability to Contain the Tissue Graft and Allow the Tissue Graft to Maintain its Shape The ability of the retainer to contain the tissue graft may be assessed by enclosing the tissue graft within the two members of the retainer and submerging the retainer and tissue graft in liquid (e.g., saline, water, lactated ringers, or dextrose), so that the liquid is fully dispersed within the two members of the retainer and the tissue graft is fully submerged. The retainer may remain static while submerged in the liquid, or it may be agitated or shaken. A visual observation may be made to determine if the tissue graft remained within the perimeter of the retainer, moved within the perimeter of the retainer, or migrated outside the perimeter of the retainer. Visual observation may also be made to determine if the tissue graft maintained its shape while contained within the retainer.

Example 3—Assessment of Cytotoxicity and Compatibility for Direct Contact with Tissue Graft The retainer may be analyzed to identify potential cytotoxic effects that may occur when the retainer is in direct or indirect contact with a patient or that may occur by migration of extractables from the retainer to the tissue graft. The analysis may be performed on a portion of the retainer or on the tissue graft after contact with the retainer utilizing methods including, but not limited to, physicochemical testing, non-volatile residue, residue on ignition, extractable metals, buffering capacity, pH, biological reactivity, identity of materials or additives by infrared spectrophotometry, ultraviolet visible spectroscopy, thermal analysis, differential scanning calorimetry, total organic carbon, acidity, alkalinity, in vitro biological reactivity by agar diffusion test, direct contact test, or elution test, in vivo biological reactivity by systemic injection test, intracutaneous test, or implantation test in which the degree of reactivity is measured on a scale of 0 to 4, where 0 indicates no reactivity and 4 indicates a severe cytotoxic reaction.

Example 4—Assessment of Ability to Withstand Cryogenic Temperature

The retainer's ability to withstand ultra low temperatures may be assessed by measuring the material strength when subjected to subzero temperatures by methods including, but not limited to, flexural strength, durability, impact strength, and dynamic mechanical analysis where the retainer is capable to withstand up to 1770 Newtons.

To further quantify the ability of the material to withstand frozen storage, multi-axial impact testing similar to ASTM D 3763 was performed at ambient and ultra low temperatures. The provided materials were cut into 4×4 inch plaque specimens. For this test method, a plunger with a steel rod is allowed to impact a test specimen, and impact data, including force, time, and deflection, is recorded using a load cell which is incorporated within the hemispherical end of the steel rod. From this data, the energy absorbed by the sample during the impact, and through failure, is determined. The results are shown in Table 1 below.

following methods, but not limited to, quantitation of adenosine triphosphate (ATP) and fluorescent staining.

In the following study, a comparison was made between a two-piece retainer design with channels and protrusions and a one-piece hinged clamshell retainer, which does not contain the channels or protrusions and creates a significantly larger clearance between the two sides. The intent was to determine the effect of the channels and the clearance between the two sides of the retainer on cell viability. Tissue samples (i.e., representing the tissue graft) were prepared and split evenly between the two test groups. Samples were processed, packaged in each respective retainer, sealed into pouches with cryoprotectant solution (i.e., cryopreservative media), cryopreserved to −100° C., and stored at −80° C. Samples were tested after the following time points: 48 hours, 2 weeks, and 1 month after cryopreservation and frozen storage. Tissue samples were then analyzed by Cell-Titer-Glo® Luminescent Cell Viability Assay (Promega, Madison, Wis.). In addition, samples were stained using ethidium homodimer-1 and calcein and viewed under fluorescence microscope.

Figure 13:
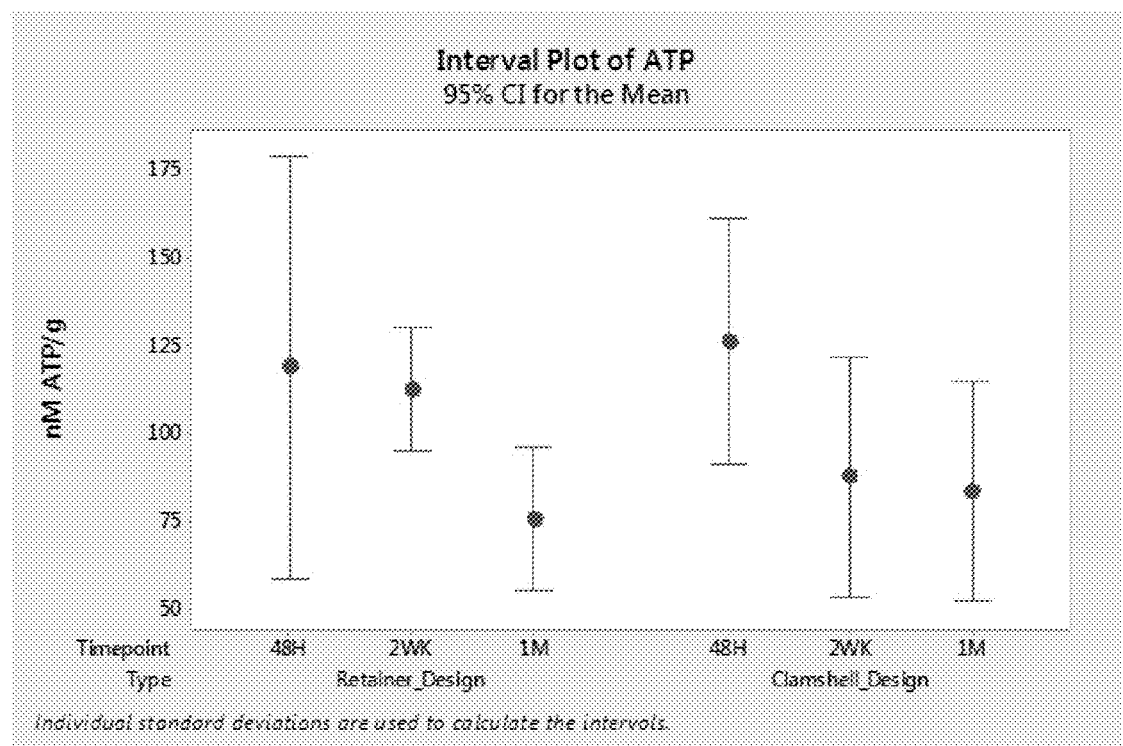
FIG. 13 is a graph showing the results of cell viability testing on the tissue graft retainer of FIG. 7 (left) and a clamshell (i.e., one piece) tissue graft retainer (right)

Using the measurement of ATP present, an analysis was made to quantify if a difference in cell viability existed between the two-piece retainer and clamshell retainer. This was done by a statistical T-test which uses a comparison of mean responses to determine if a difference exists. The results in Table 2 and FIG. 13 below show that the two-piece retainer exerts no negative effect on the viability of the cells within the tissue sample compared to the clamshell.

TABLE 2

| Analysis of Variance for Retainer Clearance Versus ATP at Final Timpoint (1 Month) | | | | | |
|---|---|---|---|---|---|
| Source | DF | ADj SS | ADj MS | F-Value | P-Value |
| Type | 1 | 150.8 | 150.8 | 0.33 | 0.582 |

Figure 14:
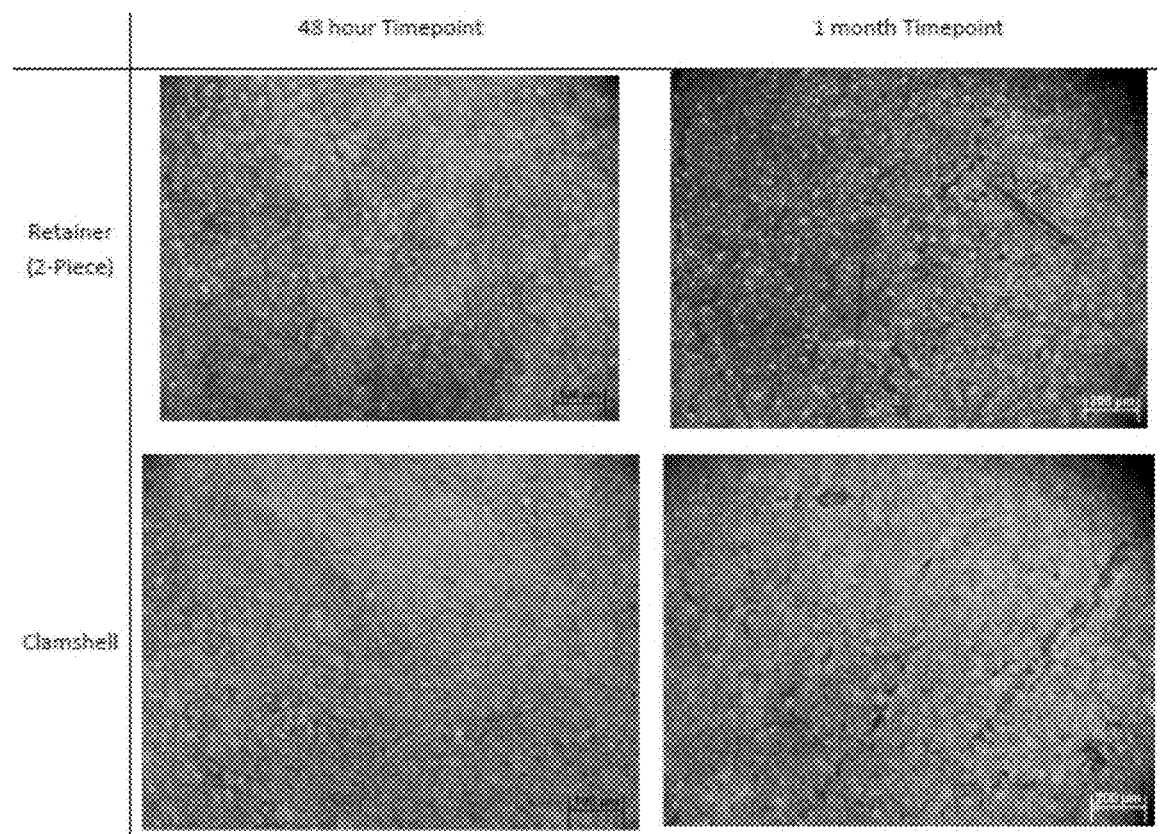
FIG. 14 is a micrograph showing the results of cell viability testing on the tissue graft retainer of FIG. 7 (top left and right) and a clamshell (i.e., one piece) tissue graft retainer (bottom left and right)

Fluorescent staining of live and dead cells was performed on both groups to qualitatively measure the effect of the channels in the retainer. If the channels were in constant contact with the tissue graft it may have affected the viability by not allowing appropriate media to reach the tissue graft. At the conclusion of the 1 month study the result showed that there was no impact made by the channels to the viability of the cells. FIG. 14 shows the 48 hour timepoint versus the 1 month timepoint for the retainer having two separate members and clamshell.

In another study, the ability of donor tissue to be cryopreserved to −100° C. while suspended in cryopreservative media contained in a retainer and pouch package and

TABLE 1

| Material | Test Temp | Energy at Peak Force (J) | Energy at 50% Peak Force (J) | Peak Force (N) | Displacement at Peak Force (mm) | Failure Mode |
|---|---|---|---|---|---|---|
| PETG | 23 C. | 9.64 (2.6%) | 14.20 (2.5%) | 1230 (0.7%) | 16.40 (1.3%) | Ductile |
| PETG | −70 C. | 8.35 (39.8%) | 9.93 (54.6%) | 1770 (12.0%) | 12.50 (16.6%) | Mixed |

Example 5—Assessment of Ability to Maintain Viability of Tissue Graft

Figure 15:
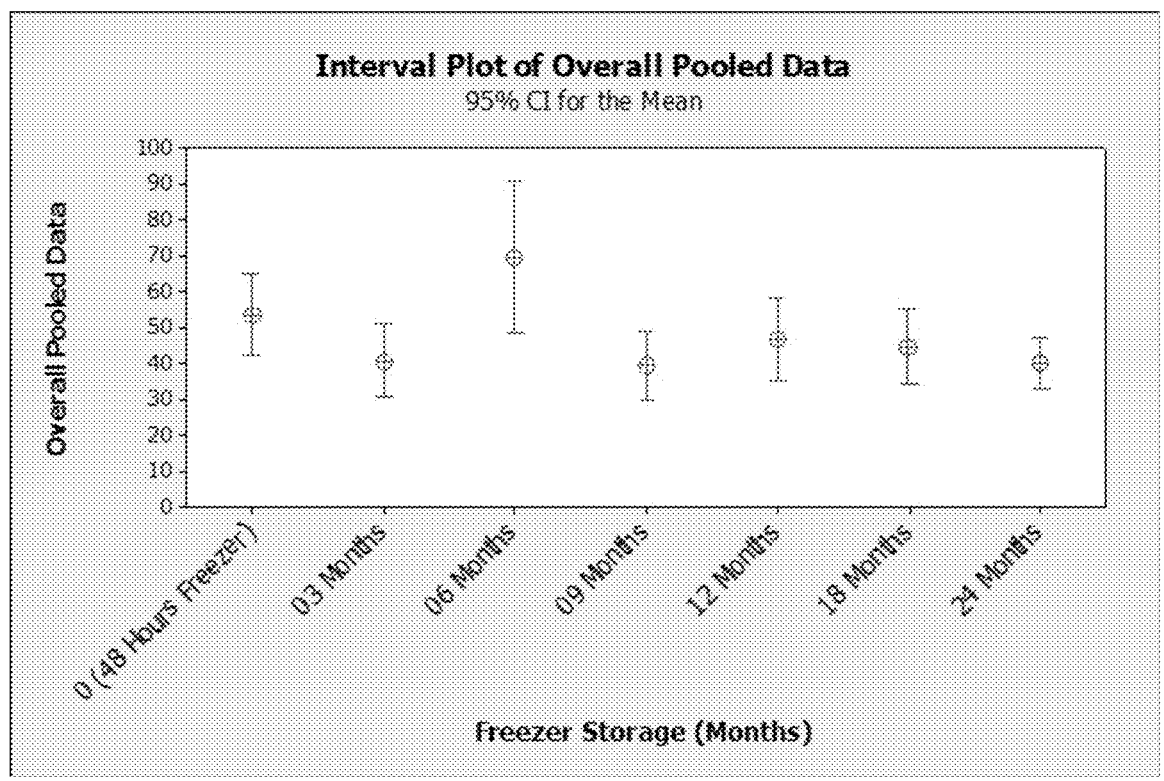
FIG. 15 is a graph showing the results of cell viability testing on the tissue graft retainer of FIG. 7, based on freezer storage times.

The retainer's ability to maintain the viability of endogenous cells in the tissue graft may be assessed by the subsequently stored in a −80° C. freezer was analyzed utilizing similar process and methods as described above. Tissue samples were analyzed over a 24 month period of frozen storage and as shown in FIG. 15, ATP levels were maintained throughout the duration of the study.

Example 6—Quantitative Assessment of the Release Force

The ability of the retainer to maintain closure is necessary to prevent migration of the tissue graft out of the retainer or during preparation for clinical use. Therefore, it is important to determine acceptability of the retainer received from a supplier prior to use. Acceptability may be determined by visual observation of the retainer's ability to remain closed after exposure to sterilization, processing, changing temperature environments and handling that may occur during packaging of tissue grafts, submersion in solution, cryopreservation, shipping, and long term storage.

In addition, the force required to engage and release the closure mechanism may be measured by force gauge or other instrument. The method employs a test fixture with mechanism to hold one member of the retainer in a fixed location and move the second member of the retainer in perpendicular direction and in parallel orientation towards the first member until the closure is fully engaged. A pre-determined compressive force is then applied for a pre-determined length of time. Next, the second member is moved away from the first member until the closure is fully released. The force required to release the closure is measured, by force gauge or other force measuring equipment.

The specified application force and minimum threshold for release force was determined by measuring the force required to engage and open parts that had been deemed unacceptable, such as not maintaining a closed system or opening after exposure to temperature changes such as cryopreservation and storage, against parts that were deemed acceptable through the same examination methods.

Figure 16:
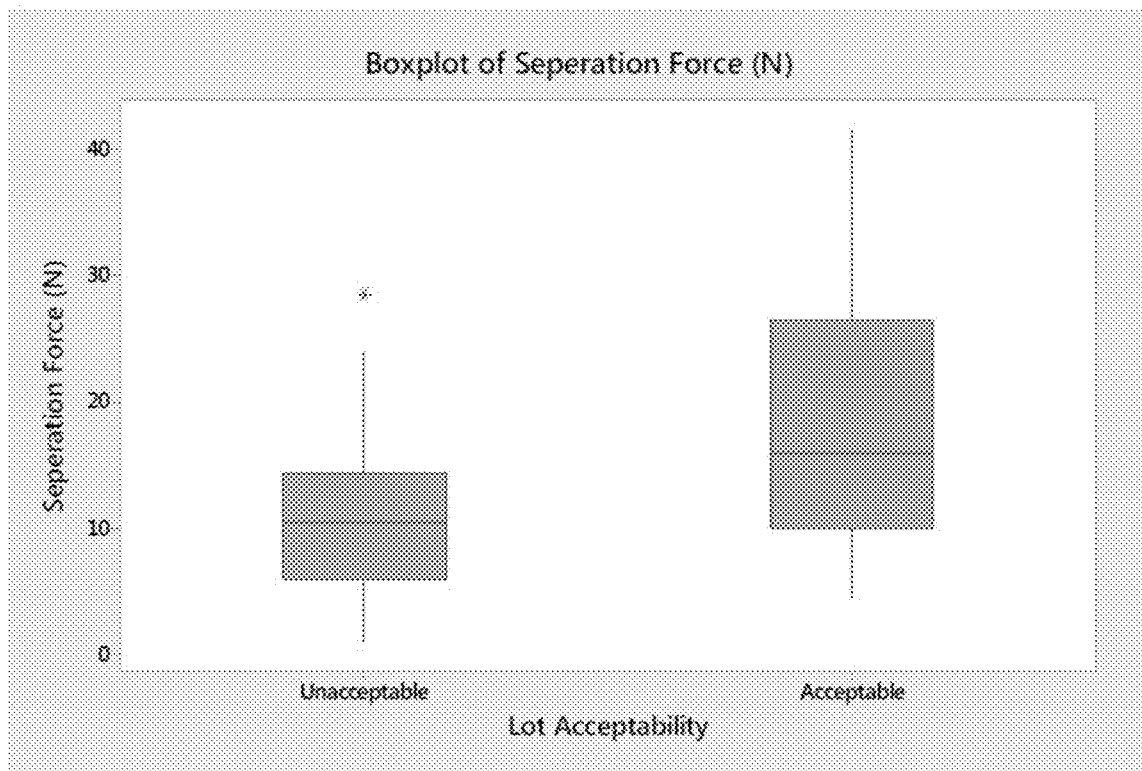
FIG. 16 is graph showing the results of studies on the separation force required for the members of the tissue graft retainer of FIG. 7.

FIG. 16 shows the mean difference between the acceptable and unacceptable parts that were measured for release force.

Figure 17:
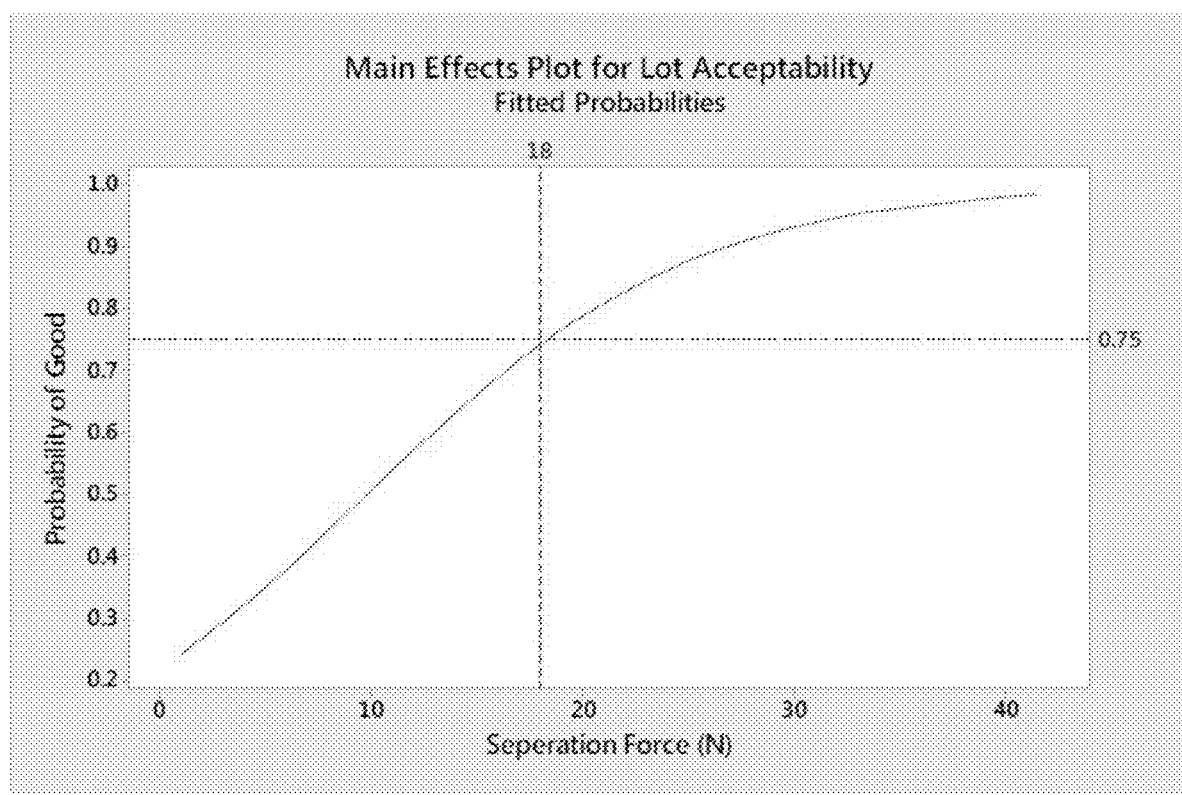
FIG. 17 is another graph showing the results of studies on the separation force required for the members of the tissue graft retainer of FIG. 7.

The data generated also provided the threshold as shown in FIG. 17. Using a Main Effects plot through a binary logistic regression, which shows the interaction between separation force and lot acceptability, a threshold limit of 18 N has at least 75% probability of identifying a potential failure before use.

The method described may be used as a Quality Control measure during the manufacture of the retainer and/or as a Quality Control measure prior to or any time after packaging the tissue graft in a closed retainer to reduce the likelihood of failures. The method may also be utilized to assess ease of opening the package when the tissue graft is prepared and used for medical treatment.

Example 7—Ability of the Channels and Inlets to Allow Flow of Cryopreservation and Rinsing Fluid The channels and inlets are intended to allow communication of cryopreservation media and the tissue graft as well as communication of a rinsing fluid and the tissue graft during static or agitated soak or by pouring or injecting fluid with syringe or other device. The amount of fluid that is exchanged is influenced by the shape, dimensions, orientation, and distribution of channels and can be assessed by a dye penetration method where the retainer is submerged in a dye solution that allows visible contrast against the retainer material, such as Toluidine Blue, and a visual observation of the direction of fluid flow and amount of fluid that is passed through the retainer can be made.

Example 8—Quantification of Residual c Cryopreservation Media Remaining after Rinsing Prior to use of the tissue graft for medical treatment, the tissue graft may be rinsed with one or more solutions including, but not limited to, Lactated Ringers in 5% dextrose saline solution, water, saline or irrigant. To provide containment and facilitate ease of use and handling of the tissue graft, it may be rinsed while contained in the retainer. Following a standard rinsing method, residual cryopreservation media remaining on the tissue graft may be quantified by methods including, but not limited to, gas chromatography, liquid chromatography, spectroscopy, or other chemical analysis methods.

In the following study, remaining levels of cryopreservation media were analyzed after rinsing by gas chromatography with a flame ionization detector. Samples from three different tissue donors were rinsed by submerging the tissue graft suspended in the retainer in Lactated Ringers in 5% dextrose saline solution for 5 minutes and comparing to non-rinsed control samples. The average level of residual cryopreservation media for samples undergoing the rinse procedure was 2.94±0.92% by weight, and the average level for samples that did not undergo the rinse procedure was 9.70±1.44% by weight. Therefore the retainer was determined to provide adequate fluid flow of the rinsing solution and cryopreservation media.

Example 9—Assessment of Optional Backing

The tissue graft may optionally be supported by and packaged with a backing to maintain its shape during cryopreservation, ensuring sufficient exposure to cryopreservation media, and to facilitate ease of application for medical treatment. Materials may be considered unsuitable if it were not biocompatible as measured by methods described in Example 3, visually damaged during sterilization, processing, freezing, or shipping, caused damage to the tissue during processing or during removal for clinical use, or has a negative effect on cell viability measured by methods described in Example 5.

Alternatively, in the following study, materials were scored on a scale of 1 to 5 for the ability to hold the tissue graft in place during processing and packaging and the ability to release the tissue graft during various anticipated clinical uses as described in Table 3. A score of 1 was regarded to completely fulfill the criteria and a score of 5 was regarded as not fulfilling the criteria. Table 3 shows resulting ranking scores for various materials.

TABLE 3

|  | Test Article | | | | | | | | |
| --- | --- | --- | --- | --- | --- | --- | --- | --- | --- |
|  | 1 | 2 | 3 | 4 | 5 | 5-2 | 6 | 7 | 8 |
| Processing Average Score | 1.00 | 1.00 | 1.67 | 1.67 | 1.00 | 1.33 | 1.58 | 2.33 | 2.00 |
| End Use Average Score | 3.25 | 3.25 | 2.50 | 2.50 | 1.38 | 1.13 | 3.00 | 2.38 | 2.75 |
| Overall Average Score | 2.13 | 2.13 | 2.00 | 2.00 | 1.19 | 1.19 | 2.22 | 2.25 | 2.25 |

We claim:

1. A tissue graft packaging system comprising:
   a retainer, said retainer including
   a first member having a first inner surface including first engagement means, a first plurality of channel sidewalls extending along said first inner surface, and a first plurality of channels defined by said first plurality of channel sidewalls, and
   a second member having a second inner surface including second engagement means configured to removeably engage said first engagement means, a second plurality of channel sidewalls extending along said second inner surface, and a second plurality of channels defined by said second plurality of channel sidewalls,
   wherein said first plurality of channel sidewalls and said second plurality of channel sidewalls are configured to form a continuous interior space between said first and second members such that, when first and second members are assembled and first and second engagement means are removeably engaged, said continuous interior space is a gap and said first and second pluralities of channel sidewalls do not contact one another.

2. The tissue graft packaging system of claim 1, wherein said first member includes a first end and an opposed second end, said first plurality of channels and said first plurality of channel sidewalls extending longitudinally between said first and second ends, and wherein said second member includes a third end and an opposed fourth end, said second plurality of channels and said second plurality of channel sidewalls extending longitudinally between said third and fourth ends.

3. The tissue graft packaging system of claim 2, wherein said first engagement means includes a first end protrusion formed on said first end and a second end recess formed in said second end, and wherein said second engagement means includes a third end protrusion formed on said third end and a fourth end recess formed in said fourth end, said first end protrusion being configured so as to insertably and removeably engage said fourth end recess, and said third end protrusion being configured so as to insertably and removeably engage said second end recess.

4. The tissue graft packaging system of claim 1, wherein said first member includes a first side having a first side inlet in fluid communication with said first plurality of channels, and an opposed second side having a second side inlet in fluid communication with said first plurality of channels, and wherein said second member includes a third side having a third side inlet in fluid communication with said second plurality of channels, and an opposed fourth side having a fourth side inlet in fluid communication with said second plurality of channels.

5. The tissue graft packaging system of claim 4, wherein said first engagement means further includes a first side protrusion formed on said first side, a first side recess formed in said first side, a second side protrusion formed on said second side and a second side recess formed in said second side, said first side inlet being located between said first side protrusion and said first side recess, and said second side inlet being located between said second side protrusion and said second side recess, and wherein said second engagement means further includes a third side protrusion formed on said third side, a third side recess formed in said third side, a fourth side protrusion formed on said fourth side and a fourth side recess formed in said fourth side, said third side inlet being located between said third side protrusion and said third side recess, and said fourth side inlet being located between said fourth side protrusion and said fourth side recess.

6. The tissue graft packaging system of claim 3, wherein said second end of said first member includes a second end raised area in which said second end recess is formed, wherein said second member has a third side and an opposed fourth side which includes a fourth side raised area, and wherein, when said first and second members are assembled together forming said retainer, said to form a first end passageway therebetween which enables cryopreservation media to flow into and out of said retainer, said first end passageway being in fluid communication with said first and second pluralities of channels.

7. The tissue graft packaging system of claim 1, wherein said first member is structurally identical to said second member.

8. The tissue graft packaging system of claim 7, wherein said first member and said second member are arranged to be symmetrical to one another, whereby said first inner surface is inverted with respect to said second inner surface.

9. The tissue graft packaging system of claim 1, wherein said first plurality of channels are evenly distributed along said first inner surface, and wherein said second plurality of channels are evenly distributed along said second inner surface.

10. The tissue graft packaging system of claim 1, wherein said first member includes first indicia and said second member includes second indicia, whereby said first and second indicia facilitate the correct alignment of said first and second members upon assembly of said retainer.

11. The tissue graft packaging system of claim 1, wherein said first and second members are made from a material that can operably withstand cryopreservation temperatures.

12. The tissue graft packaging system of claim 1, wherein said first and second members are configured and manufactured such that when secured to one another, a minimum retention force is required to maintain the interconnection of said first and second members.

13. The tissue graft packaging system of claim 12, wherein said minimum retention force is within a range of from about 5 Newtons to about 100 Newtons.

14. The tissue graft packaging system of claim 1, further comprising an inner pouch, an outer pouch and a carton, said inner pouch being sized and shaped to receive said retainer therein, said outer pouch being sized and shaped to receive said inner pouch therein, and said carton being sized and shaped to receive said outer pouch therein.

15. The tissue graft packaging system of claim 1, further comprising a tissue graft, said tissue graft being contained in said continuous interior space between said first plurality of channels and said second plurality of channels.

16. The tissue graft packaging system of claim 15, further comprising cryopreservation media, wherein said tissue graft is a cryopreserved viable tissue graft, and said retainer contains cryopreservation media within said continuous interior space, said first plurality of channels and said second plurality of channels.

17. The tissue graft packaging system of claim 15, wherein said first and second members are configured such that they minimally contact the tissue graft contained in said continuous interior space.

18. The tissue graft packaging system of claim 15, further comprising a backing maintained in contact with said tissue graft within said continuous interior space of said retainer.

19. A process for packaging, thawing and rinsing a cryopreserved viable tissue graft prior to use, said process comprising the steps of:
  (a) providing a viable tissue graft;
  (b) placing a backing on said viable tissue graft such that said backing is maintained in contact with said viable tissue graft;
  (c) providing the tissue graft packaging system of claim 1, wherein said retainer includes at least one first side passageway and at least one end passageway;
  (d) placing said viable tissue graft and said backing on said first inner surface of said first member to engage said first channel sidewalls thereof and contact said plurality of first channels;
  (e) securing said first and second members together via said first and second engagement means, whereby said viable tissue graft is contained within said continuous interior space between said first and second members, and said first and second members being configured such that they minimally contact the viable tissue graft;
  (f) introducing cryopreservation media into said retainer via said first and second pluralities of channels to immerse said viable tissue graft in said cryopreservation media;
  (g) cryopreserving said viable tissue graft;
  (h) providing said cryopreserved viable tissue graft within said tissue graft packaging system to an end user;
  (i) thawing said viable tissue graft within said retainer;
  (j) removing said cryopreservation media from said retainer via said at least one first side passageway and said at least one end passageway; and
  (k) rinsing said retainer and said viable tissue graft therein.

20. A packaged, cryopreserved viable tissue graft comprising, in combination, a cryopreserved viable tissue graft; a backing maintained in contact with said viable tissue graft; a tissue graft packaging system comprising a retainer, said retainer including a first member having a first inner surface including first engagement means, a first plurality of channel sidewalls extending along said first inner surface, and a first plurality of channels defined by said first plurality of channel sidewalls, and a second member having a second inner surface including second engagement means configured to removeably engage said first engagement means, a second plurality of channel sidewalls extending along said second inner surface, and a second plurality of channels defined by said second plurality of channel sidewalls, wherein said first plurality of channel sidewalls and said second plurality of channel sidewalls are configured to create a continuous interior space which is a gap between said first and second members such that said first and second pluralities of channel sidewalls do not contact one another, said continuous interior space containing said viable tissue graft and said backing therein; and cryopreservation media contained within said continuous interior space, said first plurality of channels and said second plurality of channels.

21. A tissue graft packaging system comprising: a retainer, said retainer including:
  a first member including a first inner surface including first engagement means, a first plurality of channel sidewalls extending along said first inner surface, and a first plurality of channels defined by said first plurality of channel sidewalls; and
  a second member including a second inner surface including second engagement means configured to removeably engage said first engagement means, a second plurality of channel sidewalls extending along said second inner surface, and a second plurality of channels defined by said second plurality of channel sidewalls, wherein said first plurality of channel sidewalls and said second plurality of channel sidewalls are configured to form a continuous interior space between said first and second members;
wherein said first member further includes a first side having a first side inlet in fluid communication with said first plurality of channels, and an opposed second side having a second side inlet in fluid communication with said first plurality of channels; and
wherein second member further includes a third side having a third side inlet in fluid communication with said second plurality of channels, and an opposed fourth side having a fourth side inlet in fluid communication with said second plurality of channels.

22. The tissue graft packaging system of claim 21, wherein said first member includes a first end and an opposed second end, said first plurality of channels and said first plurality of channel sidewalls extending longitudinally between said first and second ends, and wherein said second member includes a third end and an opposed fourth end, said second plurality of channels and said second plurality of channel sidewalls extending longitudinally between said third and fourth ends.

23. The tissue graft packaging system of claim 22, wherein said first engagement means includes a first end protrusion formed on said first end and a second end recess formed in said second end, and wherein said second engagement means includes a third end protrusion formed on said third end and a fourth end recess formed in said fourth end, said first end protrusion being configured so as to insertably and removeably engage said fourth end recess, and said third end protrusion being configured so as to insertably and removeably engage said second end recess.

24. The tissue graft packaging system of claim 21, wherein said first engagement means further includes a first side protrusion formed on said first side, a first side recess formed in said first side, a second side protrusion formed on said second side and a second side recess formed in said second side, said first side inlet being located between said first side protrusion and said first side recess, and said second side inlet being located between said second side protrusion and said second side recess, and wherein said second engagement means further includes a third side protrusion formed on said third side, a third side recess formed in said third side, a fourth side protrusion formed on said fourth side and a fourth side recess formed in said fourth side, said third side inlet being located between said third side protrusion and said third side recess, and said fourth side inlet being located between said fourth side protrusion and said fourth side recess.

25. The tissue graft packaging system of claim 23, wherein said second end of said first member includes a second end raised area in which said second end recess is formed, wherein said second member has a third side and an opposed fourth side which includes a fourth side raised area, and wherein, when said first and second members are assembled together forming said retainer, said to form a first end passageway therebetween which enables cryopreservation media to flow into and out of said retainer, said first end passageway being in fluid communication with said first and second pluralities of channels.

26. The tissue graft packaging system of claim 21, wherein said first member is structurally identical to said second member.

27. The tissue graft packaging system of claim 26, wherein said first member and said second member are arranged to be symmetrical to one another, whereby said first inner surface is inverted with respect to said second inner surface.

28. The tissue graft packaging system of claim 21, wherein said first plurality of channels are evenly distributed along said first inner surface, and wherein said second plurality of channels are evenly distributed along said second inner surface.

29. The tissue graft packaging system of claim 21, wherein said first member includes first indicia and said second member includes second indicia, whereby said first and second indicia facilitate the correct alignment of said first and second members upon assembly of said retainer.

30. The tissue graft packaging system of claim 21, wherein said first and second members are made from a material that can operably withstand cryopreservation temperatures.

31. The tissue graft packaging system of claim 21, wherein said first and second members are configured and manufactured such that when secured to one another, a minimum retention force is required to maintain the interconnection of said first and second members.

32. The tissue graft packaging system of claim 31, wherein said minimum retention force is within a range of from about 5 Newtons to about 100 Newtons.

33. The tissue graft packaging system of claim 21, further comprising an inner pouch, an outer pouch and a carton, said inner pouch being sized and shaped to receive said retainer therein, said outer pouch being sized and shaped to receive said inner pouch therein, and said carton being sized and shaped to receive said outer pouch therein.

34. The tissue graft packaging system of claim 21, further comprising a tissue graft, said tissue graft being contained in said continuous interior space between said first plurality of channels and said second plurality of channels.

35. The tissue graft packaging system of claim 34, further comprising cryopreservation media, wherein said tissue graft is a cryopreserved viable tissue graft, and said retainer contains cryopreservation media within said continuous interior space, said first plurality of channels and said second plurality of channels.

36. The tissue graft packaging system of claim 34, wherein said first and second members are configured such that they minimally contact the tissue graft contained in said continuous interior space.

37. The tissue graft packaging system of claim 34, further comprising a backing maintained in contact with said tissue graft within said continuous interior space of said retainer.

38. A packaged, cryopreserved viable tissue graft comprising, in combination:
    a cryopreserved viable tissue graft;
    a backing maintained in contact with said viable tissue graft;
    a tissue graft packaging system comprising a retainer which includes:
        a first member including:
            a first inner surface which includes first engagement means,
            a first plurality of channel sidewalls extending along said first inner surface,
            a first plurality of channels defined by said first plurality of channel sidewalls,
            a first side having a first side inlet in fluid communication with said first plurality of channels, and
            an opposed second side having a second side inlet in fluid communication with said first plurality of channels;
        a second member including:
            a second inner surface having second engagement means configured to removeably engage said first engagement means,
            a second plurality of channel sidewalls extending along said second inner surface,
            a second plurality of channels defined by said second plurality of channel sidewalls,
            a third side having a third side inlet in fluid communication with said second plurality of channels, and
            an opposed fourth side having a fourth side inlet in fluid communication with said second plurality of channels,
        wherein said first plurality of channel sidewalls of said first member and said second plurality of channel sidewalls of said second member are configured to create a continuous interior space between said first and second members, said continuous interior space containing said viable tissue graft and said backing therein; and
    cryopreservation media contained within said continuous interior space, said first plurality of channels and said second plurality of channels.

39. A method for using the packaged, cryopreserved viable tissue graft of claim 38 to treat tissue of a subject, comprising the steps of:
    (a) thawing said viable tissue graft while within said retainer;
    (b) removing said cryopreservation media from said retainer via said at least one first side passageway and said at least one end passageway;
    (c) rinsing said retainer and said viable tissue graft therein;
    (d) separating said first and second members of said retainer and removing said viable tissue graft; and
    (e) placing said viable tissue graft in contact with the tissue.

40. A process for providing a packaged, cryopreserved viable tissue graft, said process comprising the steps of:
    (a) providing a viable tissue graft;
    (b) placing a backing on said viable tissue graft such that said backing is maintained in contact with said viable tissue graft;
    (c) providing the tissue graft packaging system of claim 21, wherein said retainer includes at least one first side passageway and at least one end passageway;
    (d) placing said viable tissue graft and said backing on said first inner surface of said first member to engage said first channel sidewalls thereof and contact said plurality of first channels;
    (e) securing said first and second members together via said first and second engagement means, whereby said viable tissue graft is contained within said continuous interior space between said first and second members, and said first and second members being configured such that they minimally contact the viable tissue graft;
    (f) introducing cryopreservation media into said retainer via said first and second pluralities of channels to immerse said viable tissue graft in said cryopreservation media; and
    (g) cryopreserving said viable tissue graft.

* * * * *